US012741030B2

(12) United States Patent
Choi et al.

(10) Patent No.: US 12,741,030 B2

(45) **Date of Patent: *Sep. 22, 2026**

(54) VANILLIN DERIVATIVE COMPOUNDS INDUCING SELECTIVE DEGRADATION OF PLK1

(71) Applicant: UPPTHERA, Incheon (KR)

(72) Inventors: Si Woo Choi, Incheon (KR); Soo Hee Ryu, Incheon (KR); Ji Hoon Ryu, Seoul (KR); San Ha Son, Incheon (KR); Hwa Jin Lee, Incheon (KR); Seong Hoon Kim, Incheon (KR); Boas Nam, Incheon (KR); Im Suk Min, Gyeonggi-do (KR); Hye Guk Ryu, Incheon (KR); Keum Young Kang, Incheon (KR)

(73) Assignee: UPPTHERA, Incheon (KR)

(*) Notice: Subject to any disclaimer, the term of this patent is extended or adjusted under 35 U.S.C. 154(b) by 795 days.

This patent is subject to a terminal disclaimer.

(21) Appl. No.: 17/914,574

(22) PCT Filed: Mar. 27, 2021

(86) PCT No.: PCT/KR2021/003808

§ 371 (c)(1),
(2) Date: Sep. 26, 2022

(87) PCT Pub. No.: WO2021/194319

PCT Pub. Date: Sep. 30, 2021

(65) Prior Publication Data

US 2023/0203006 A1 Jun. 29, 2023

(30) Foreign Application Priority Data

Mar. 27, 2020 (KR) ........................ 10-2020-0037875

(51) Int. Cl.

| | |
|---|---|
| ***A61K 47/55*** | (2017.01) |
| ***A61K 47/54*** | (2017.01) |
| ***C07D 401/14*** | (2006.01) |
| ***C07D 409/14*** | (2006.01) |
| ***C07D 417/14*** | (2006.01) |

(52) U.S. Cl.

CPC ............ *A61K 47/55* (2017.08); *A61K 47/545* (2017.08); *C07D 401/14* (2013.01); *C07D 409/14* (2013.01); *C07D 417/14* (2013.01)

(58) Field of Classification Search

CPC .... A61K 47/55; A61K 47/545; A61K 31/454; A61K 31/519; C07D 401/14; C07D 409/14; C07D 417/14; C07D 487/04; C07D 519/00; A61P 35/00; A61P 25/00; A61P 25/08; A61P 25/14; A61P 25/16; A61P 25/28; A61P 35/02; C07K 5/06034

See application file for complete search history.

(56) References Cited

U.S. PATENT DOCUMENTS

| | | | | |
|---|---|---|---|---|
| 11,833,208 B2 * | 12/2023 | Choi | .................... | C07D 417/14 |
| 2025/0114460 A1 * | 4/2025 | Ryu | ........................ | A61P 35/00 |

FOREIGN PATENT DOCUMENTS

| | | | |
|---|---|---|---|
| CN | 106543185 | 3/2017 | |
| CN | 106977584 | 7/2017 | |
| CN | 109879877 | 6/2019 | |
| KR | 10-2010-0087292 | 9/2008 | |
| KR | 10-2017-0002446 | 1/2017 | |
| KR | 10-2018-0011759 | 2/2018 | |
| KR | 10-2019-0116315 | 10/2019 | |
| KR | 10-2020-0032453 | 3/2020 | |
| WO | WO-2008113711 A1 * | 9/2008 | ........... C07D 471/18 |
| WO | WO 2009/153197 | 12/2009 | |
| WO | WO2017/079267 | 5/2017 | |

OTHER PUBLICATIONS

"Development and Characterization of a Wee1 Kinase Degrader" Z Li, BJ Pinch, CM Olson, KA Donovan, RP Nowak, CE Mills, DA Scott, ZM Doctor, NA Eleuteri, M Chung, PK Sorger, ES Fischer, NS Gray Cell Chem Biol 27(1):57, p. 57-65 (Year: 2019).*

"Biological impact of freezing Plk1 in its inactive conformation in cancer cells" S Keppner, E Proschak, M Kaufmann, K Strebhardt, G Schneider, and B Spänkuch, B. Cell Cycle, 9(4), p. 761-774 (Year: 2010).*

American Cancer Society. Cancer Risk and Prevention. https://www.cancer.org/cancer/risk-prevention.html (Year: 2024).*

"Biomarkers in precision cancer immunotherapy: Promise and challenges. American Society of Clinical Oncology" WB Mckean, JC Moser, D Rimm, and S Hu-Lieskovan Educational Book (2020), 40, p. e275-e291 (Year: 2020).*

"Polo-like kinase 1 (PLK1) signaling in cancer and beyond" S Iliaki, R Beyaert, IS Afonina Biochemical Pharmacology vol. 193, 1147447 (Year: 2021).*

Akuffo et al., "Ligand-mediated protein degradation reveals functional conservation among sequence variants of the CUL4-type E3 ligase substrate receptor cereblon," 293(16): P6187-6200, Apr. 2018.

Bolden et al., "Inducible In Vivo Silencing of Brd4 Identifies Potential Toxicities of Sustained BET Protein Inhibition," *Cell Reports,* 8(6): 1919-1929, Sep. 18, 2014.

Buckley et al., "Small-Molecule Inhibitors of the Interaction Between the E3 Ligase VHL and HIF1α," *Angewandte Chemie Int. Ed.,* 51(46): 11463-11467, Oct. 12, 2012.

Buckley et al., "Targeting the von Hippel-Lindau E3 Ubiquitin Ligase Using Small Molecules To Disrupt the VHL/HIF-1α Interaction," *J. Am. Chem. Soc.,* 134(10): 4465-4468, Feb. 27, 2012.

(Continued)

*Primary Examiner* — Kara R. Mcmillian

*Assistant Examiner* — Sophia P Hirakis

(74) *Attorney, Agent, or Firm* — Klarquist Sparkman, LLP

(57) ABSTRACT

The present invention provides novel compounds that induce selective polo-like kinase 1 (PLK1) degradation. Specifically, the present invention provides a bifunctional compound in which a PLK1 binding moiety and an E3 ubiquitin ligase-binding moiety are linked by a chemical linker. The present invention provides the compound, a method for preparing the same, and the use thereof. The compounds may be effectively utilized for preventing or treating PLK1 related diseases.

3 Claims, No Drawings

(56) References Cited

OTHER PUBLICATIONS

Burslem et al., "Efficient Synthesis of Immunomodulatory Drug Analogues Enables Exploration of Structure-Degradation Relationships," *Chem Med Chem,* 13(15): 1508-1512, Jun. 5, 2018.
Burslem et al., "Small-Molecule Modulation of Protein Homeostasis," *Chem. Rev.,* 117(17): 11269-11301, Aug. 4, 2017.
Chamberlain et al., "Cereblon modulators: Low molecular weight inducers of protein degradation," *Drug Discovery Today: Technologies,* vol. 31, pp. 29-34, Mar. 13, 2019.
Galdeano et al., "Structure-Guided Design and Optimization of Small Molecules Targeting the Protein-Protein Interaction between the von Hippel-Lindau (VHL) E3 Ubiquitin Ligase and the Hypoxia Inducible Factor (HIF) Alpha Subunit with in Vitro Nanomolar Affinities," *J. Med. Chem.,* 57(20): 8657-8663, Oct. 6, 2014.
Gheghiani et al., "PLK1 Activation in Late G2 Sets Up Commitment to Mitosis," *Cell Reports,* vol. 19, pp. 2060-2073, Jun. 6, 2017.
International Search Report and Written Opinion issued for International Application No. PCT/KR2021/003808 on Jul. 6, 2021.
Ito et al., "Identification of a Primary Target of Thalidomide Teratogenicity," *Science,* 327(5971): 1345-1350, Mar. 12, 2010.
Keppner et al., "Identification and Validation of a Potent Type II Inhibitor of Inactive Polo-like Kinase 1," *ChemMedChem,* 4(11): 1806-1809, Oct. 23, 2009.
Mu et al., "Protein targeting chimeric molecules specific for dual bromodomain 4 (BRD4) and Polo-like kinase 1 (PLK1) proteins in acute myeloid leukemia cells," *Biochemical and Biophysical Research Communications,* 521(4): 833-839, Nov. 7, 2019.
Rodriguez-Gonzalez et al., "Targeting steroid hormone receptors for ubiquitination and degradation in breast and prostate cancer," *Oncogene,* vol. 27, pp. 7201-7211, Sep. 15, 2008.
Schneekloth et al., "Chemical Genetic Control of Protein Levels: Selective in Vivo Targeted Degradation," *J. Am. Chem. Soc.,* 126(12): 3748-3754, Mar. 1, 2004.
Soares et al., "Group-Based Optimization of Potent and Cell-Active Inhibitors of the von Hippel-Lindau (VHL) E3 Ubiquitin Ligase: Structure-Activity Relationships Leading to the Chemical Probe (2S,4R)-1-((S)-2-(1-Cyanocyclopropanecarboxamido)-3,3-dimethylbutanoyl)-4-hydroxy-N-(4-(4-methylthiazol-5-yl)benzyl)pyrrolidine-2-carboxamide (VH298)," *J. Med. Chem.,* 61(2): 599-618, Sep. 18, 2017.
Bondeson et al., "Lessons in PROTAC design from selective degradation with a promiscuous warhead," *Cell Chem Biol.,* 25(1):78-87 (Jan. 18, 2018) published online Nov. 9, 2017.
Chan et al., "Impact of Target Warhead and Linkage Vector on Inducing Protein Degradation: Comparison of Bromodomain and Extra-Terminal (BET) Degraders Derived from Triazolodiazepine (JQ1) and Tetrahydroquinoline (I-BET726) BET Inhibitor Scaffolds," *J. Med. Chem.,* 61(2):504-513 (Jan. 25, 2018) published online Jun. 22, 2017.
Dong et al., "Characteristic roadmap of linker governs the rational design of PROTACs," *Acta Pharmaceutica Sinica B,* 14(10):4266-4295 (Oct. 2024) published online Apr. 11, 2024.
Jaeger et al., "Expanding the Degradable Proteome: Designing PROTACs by the Book," *Cell Chemical Biology,* 27(1):14-16 (Jan. 16, 2020).
Wright et al., "Dual Targeting of WEE1 and PLK1 by AZD1775 Elicits Single Agent Cellular Anticancer Activity," *ACS Chem. Biol,* 12(7):1883-1892 (Jul. 21, 2017) published online Jun. 7, 2017.

* cited by examiner

VANILLIN DERIVATIVE COMPOUNDS INDUCING SELECTIVE DEGRADATION OF PLK1

CROSS REFERENCE TO RELATED APPLICATIONS

This is the U.S. National Stage of International Application No. PCT/KR2021/003808, filed Mar. 27, 2021, which was published in English under PCT Article 21(2), which in turn claims the benefit of KR Application No. 10-2020-0037875, filed Mar. 27, 2020, which is incorporated herein by reference in its entirety.

TECHNICAL FIELD

The present invention relates to a selective PLK1 degradation inducing compound, a method for preparing the same, and the use thereof.

BACKGROUND ART

Polo-like kinase 1 (PLK1) is a serine/threonine kinase involved in the conversion of G2/M phase during cell growth and division. PLK1 is expressed and activated in a pulse form from the S phase to the G2/M phase, and rapidly degrades as mitosis ends.

PLK1 is overexpressed in various carcinomas such as colon cancer, lung cancer, bladder cancer, and melanoma, etc., and cancer cells overexpressing PLK1 tend to show resistance to various types of anticancer drugs. As the PLK1 dependence in various carcinomas was revealed as described above, there have been attempts to develop PLK1 inhibitor compounds such as volasertib (also known as BI6727), etc.

However, the conventional PLK1 inhibitors do not sufficiently inhibit PLK1 activity at concentrations that are clinically safe. Thus, there is a problem that even if the cell cycle of cancer cells is temporarily delayed, some cancer cells eventually restart the cell cycle, which may not obtain sufficient clinical effects (see Gheghiani et al., Cell Reports, 2017, etc.). In fact, many pharmaceutical companies such as Boehringer Ingelheim, GlaxoSmithKline, etc., have attempted to develop small-molecular compound-based PLK1 inhibitors, but most of them have failed or stopped in the clinical trial stage, and thus there are no commercially available PLK1 inhibitors to date. It shows that pharmacological mechanism that follows the method of inhibiting enzyme activity by binding to the active site of PLK1 like the small molecule compound inhibitors is not sufficiently effective in the development of new drugs intended to derive anticancer effects by inhibiting PLK1 activity of cancer cells.

Recently, a proteolysis targeting chimera (PROTAC) has been proposed as a small molecule-based platform technology capable of inducing proteolysis of a target protein in the body. The PROTAC is a bifunctional compound in which a ligand molecule that binds to disease-related target protein and an E3 ubiquitin ligase binding moiety are linked by a chemical linker. Theoretically, the PROTAC compound is capable of inducing degradation of the target protein by placing the disease-related target protein near the E3 ubiquitin ligase.

DISCLOSURE OF INVENTION

Technical Problem

An object of the present invention is to provide selective PLK1 degradation inducing compounds.

Another object of the present invention is to provide a method for preparing the compounds.

Still another object of the present invention is to provide a use of the compounds.

Solution to Problem

Selective PLK1 Degradation Inducing Compounds

The present invention provides novel compounds that induce selective polo-like kinase 1 (PLK1) degradation. Specifically, the present invention provides a bifunctional compound in which a PLK1 binding moiety and an E3 ubiquitin ligase-binding moiety are linked by a chemical linker.

In one general aspect, there is provided a compound represented by the following Formula I, a stereoisomer thereof or a pharmaceutically acceptable salt thereof:

[Formula I]

ULM—Linker—PTM in the Formula I above,

ULM is CRBN E3 ubiquitin ligase binding moiety represented by the following Formula A:

[Formula A]

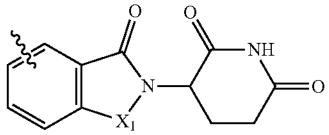

wherein $X_1$ is —$CH_2$— or —CO—;

PTM is PLK1 binding moiety represented by the following Formula II:

[Formula II]

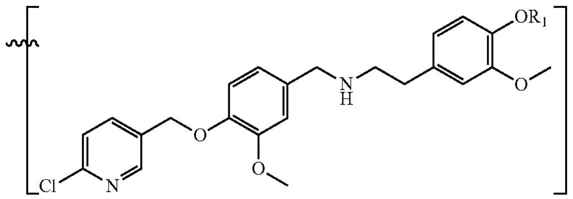

in the Formula II above, $R_1$ is $CH_3$ or ~~~~; and

Linker is a chemical group that links ULM and PTM.

In the Formula A, — indicates a covalent bond that links ULM into Linker.

In the Formula II, — indicates a covalent bond that links PTM into Linker.

(1) E3 Ubiquitin Ligase Binding Moiety (ULM)

In one embodiment of the present invention, ULM is a CRBN E3 ubiquitin ligase binding moiety represented by Formula A.

In the present invention, CRBN means Cereblon E3 ubiquitin ligase. CRBN constitutes an E3 ubiquitin ligase complex together with DDB1, Cul4A and ROC1, wherein the CRBN is a substrate recognition subunit of the complex. Some compounds capable of binding to the CRBN E3 ubiquitin ligase are known in the art. For example, after it was known that thalidomide binds to the CRBN E3 ubiquitin ligase (see Ito et al. 2010), it has been reported that a number of immunomodulatory imide drugs (IMiD) including lenalidomide and pomalidomide have CRBN binding ability (see Chamberlain and Brian. 2019; Akuffo et al. 2018; and Burslem et al. 2018, etc.).

In Formula I of the present invention, the ULM moiety represented by the Formula A is covalently linked to the Linker as defined in Formula I through ∿∿.

(2) Protein Target Moiety (PTM)

In the compound represented by Formula I, the PTM, a moiety that performs a target protein ligand function, is a polo-like kinase 1 (PLK1) binding moiety represented by Formula II above.

The compound represented by Formula II alone is a vanillin derived compound that may bind to the active site of PLK1 (see Carrasco-Gomez, Roberto, et al. *Bioorganic & medicinal chemistry letters* 24.21 (2014): 5063-5069; etc.)

In one embodiment of Formula I of the present invention, Formula II is selected from the group consisting of the following moieties:

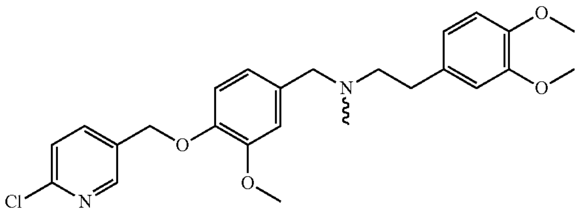

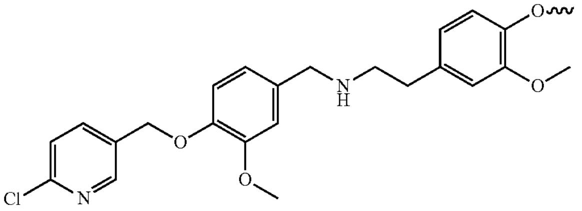

In Formula I of the present invention, the PTM moiety represented by the Formula II is covalently linked to the Linker as defined in Formula I through ∿∿.

(3) Linker

In one embodiment of the present invention, the Linker as defined in Formula I is represented by the following Formula L:

[Formula L]

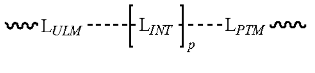

wherein:

∿∿ and – – – – – are each independently bond;

$L_{ULM}$ is covalently bonded to ULM moiety through ∿∿ that is linked thereto, $L_{PTM}$ is covalently bonded to PTM moiety through ∿∿ that is linked thereto, $L_{ULM}$ and $L_{PTM}$ are each independently a single bond, $-CH_2-$, $-NH-$, $-O-$, $-CO-$, $-CONH-$ or $-NHCO-$, $L_{INT}$ is selected from the group consisting of $-CH_2-$, $-CH_2CH_2-$, $-CHCH-$, $-CC-$, $-CH_2CH_2O-$, $-OCH_2CH_2-$, $-CH_2CH_2S-$, $-SCH_2CH_2-$, $-COO-$, $-CONH-$, $-NHCO-$ and

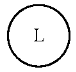

{wherein

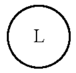

is 3-10 membered heterocycloalkyl, 6-10 membered aryl, or 5-10 membered heteroaryl}; and p is an integer between 1 to 10.

In one embodiment, Linker is a linker that is included in the compound selected from the group consisting of Compound 1 to 6.

In a certain embodiment of the present invention, the compound represented by Formula I is a compound that is selected from the group consisting of Compound 1 to 6.

In the present invention, a pharmaceutically acceptable salt refers to any organic or inorganic acid addition salt with a concentration that is relatively non-toxic, is harmless, and has effective action to patients, wherein side effects caused by this salt does not deteriorate beneficial efficacy of the compound represented by Formula I. For example, the pharmaceutically acceptable salt may be an inorganic acid such as hydrochloric acid, phosphoric acid, sulfuric acid, nitric acid, or the like, or an organic acid such as methanesulfonic acid, p-toluenesulfonic acid, acetic acid, trifluoroacetic acid, maleic acid, succinic acid, oxalic acid, benzoic acid, tartaric acid, fumaric acid, manderic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid or hydroiodic acid, but is not limited thereto.

Method for the Preparing the Selective PLK1 Degradation Inducing Compounds

In the present invention, the compound represented by Formula I above, a stereoisomer thereof, or a pharmaceutically acceptable salt thereof may be prepared through reactions such as the following Reaction Schemes 1 to 3 by a synthetic method known in the field of organic chemistry or a modification technique apparent to those skilled in the art.

[Reaction Scheme 1]

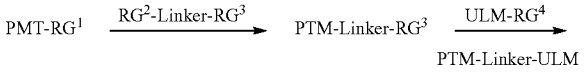

[Reaction Scheme 2]

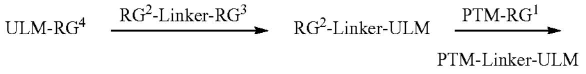

[Reaction Scheme 3]

(i)

$$\text{PMT-RG}^1 \xrightarrow{\text{RG}^{2a}\text{-Linker 1-RG}^{2b}} \text{PTM-Linker 1-RG}^{2b}$$

(ii)

$$\text{ULM-RG}^4 \xrightarrow{\text{RG}^{3a}\text{-Linker 2-RG}^{3b}} \text{RG}^{3a}\text{-Linker 2-ULM}$$

(iii)

$$\text{PTM-Linker 1-RG}^{2b} + \text{RG}^{3a}\text{-Linker 2-ULM} \longrightarrow \text{PTM-Linker 1-Linker 2-ULM} \longrightarrow \text{PTM-Linker-ULM}$$

In the Reaction Schemes 1 to 3 above, PTM, Linker and ULM are a group defined in the above, or a suitable derivative thereof. $RG^1$, $RG^2$, $RG^{2a}$, $RG^{2b}$, $RG^3$, $RG^{3a}$, $RG^{3b}$ and $RG^4$ are moieties including a suitable reactive group capable of linking together with an intermediate of the PROTAC compound represented by Formula I through formation of the covalent bond in the field of organic synthesis. The formation of the covalent bond may be achieved by synthetic reactions such as amide formation, ester formation, carbamate formation, urea formation, ether formation, amine formation, and single bonds, double bond formation between various carbons, click chemistry and the like, depending on specific reaction groups, but is not limited thereto.

Variations of each step in the above Reaction Scheme may include one or multiple synthesis steps. Isolation and purification of the product may be accomplished by standard procedures known to those skilled in the art of organic chemistry.

An example of Reaction Scheme 1 above is represented by the following scheme, including Example 5:

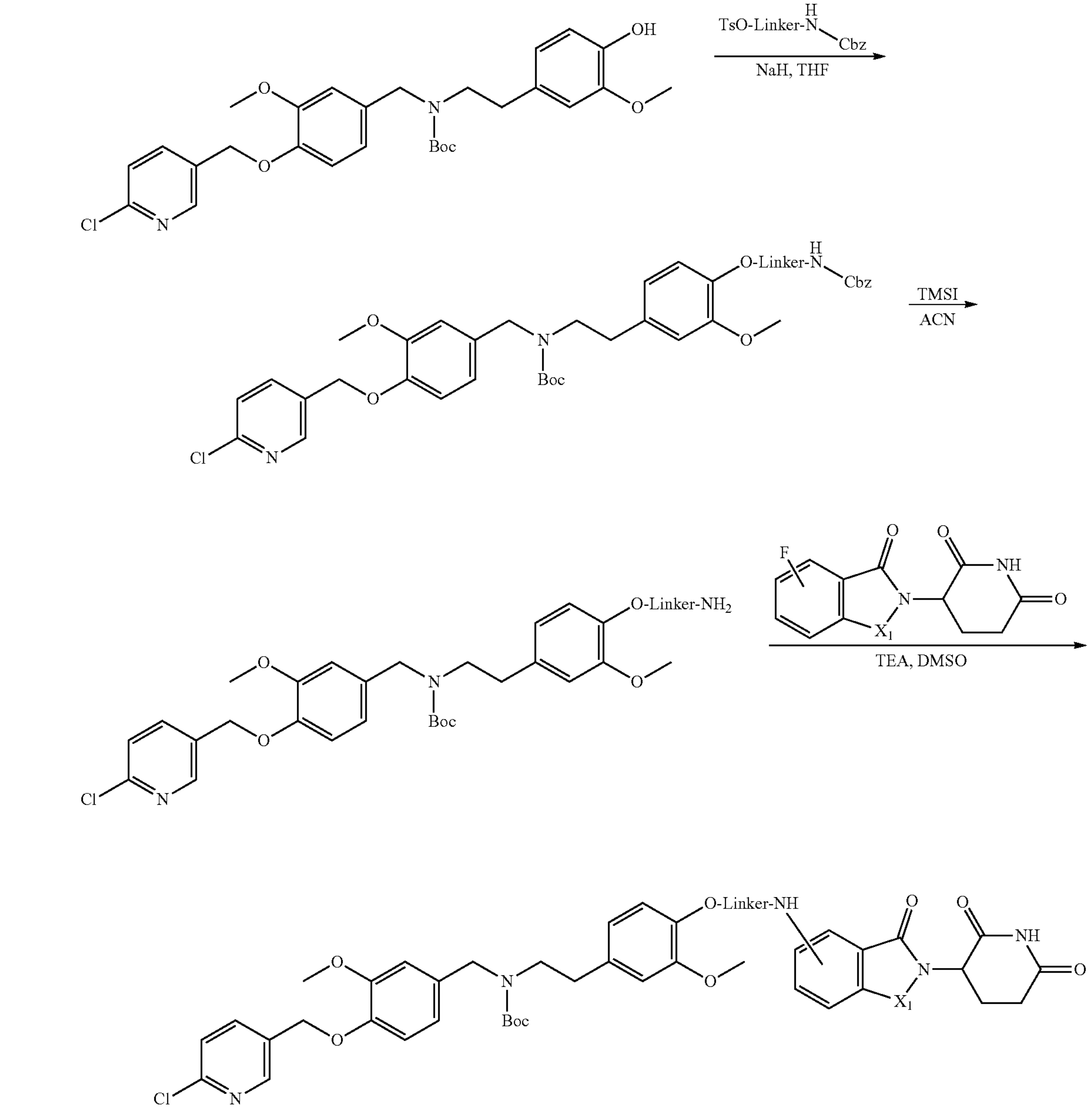

An example of Reaction Scheme 2 above is represented by the following scheme, including Example 1-4 and 6:

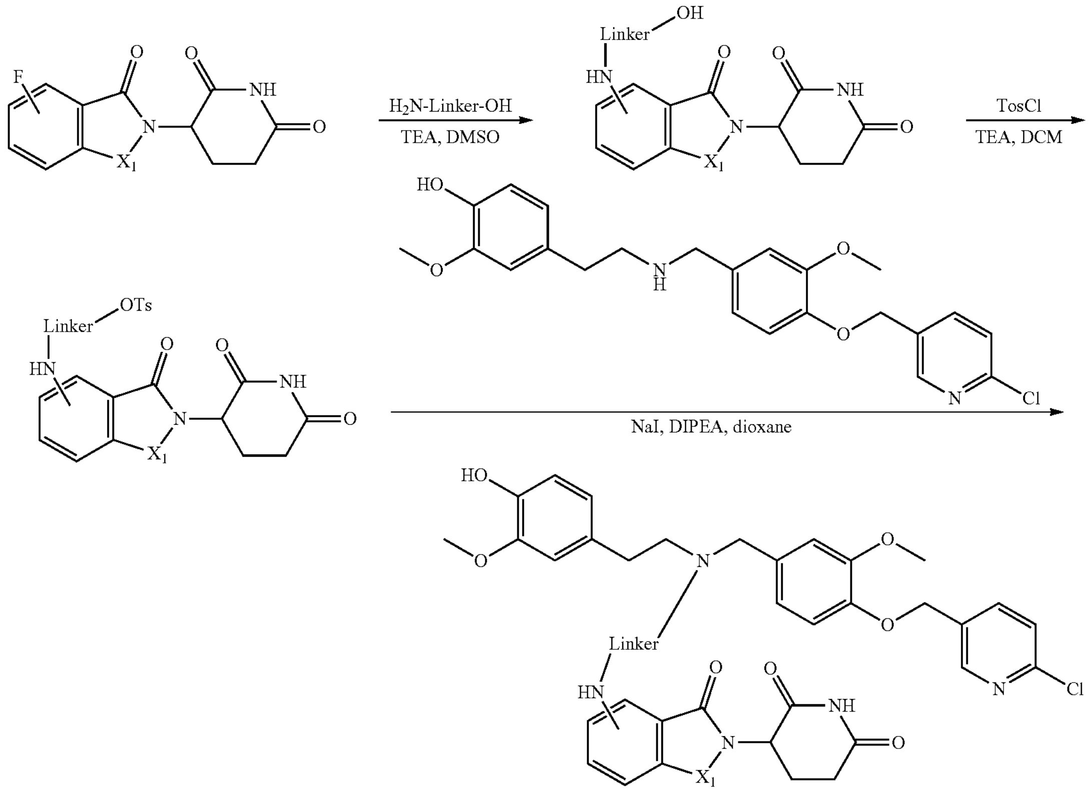

In the above Reaction Scheme, each compound represented by PTM and ULM may be synthesized by a person skilled in the art with reference to documents known in the field of organic chemistry, descriptions of Examples of the present invention, and the like.

The present invention also provides the compounds represented by PTM-Linker-RG 3 or PTM-Linker 1-$RG^{2b}$ that are the reaction intermediates of the compounds represented by Formula I.

Use of the Selective PLK1 Degradation Inducing Compounds

An embodiment of the present invention is a composition for inducing PLK1 degradation including a compound represented by Formula I or a pharmaceutically acceptable salt thereof. The Formula I is the same as defined above.

The PLK1 degradation-inducing PROTAC compound of the present invention is capable of fundamentally degrading the target protein, PLK1 in view of the mechanism of action, thereby achieving an excellent PLK1 inhibitory effect as compared to the conventional PLK1 small molecule inhibitor that inhibits the simple activity of PLK1.

Accordingly, the composition including the compound represented by Formula I of the present invention or a pharmaceutically acceptable salt thereof may be effectively employed for selective degradation of PLK1.

An embodiment of the present invention is a composition for preventing or treating PLK1-related diseases including the compound represented by Formula I or the pharmaceutically acceptable salt thereof. An another embodiment of the present invention is a method for the prevention or treatment of PLK-related diseases comprising administering the composition to a subject in need thereof. The Formula I is the same as defined above.

In the present invention, the PLK1-related disease refers to any disease or condition capable of being treated, alleviated, delayed, inhibited or prevented from induction of degradation or inhibition of activity of PLK1. In an embodiment, the PLK1-related disease may be a cancer (malignant tumor), a benign tumor, a neurological disease, or other genetic or non-genetic diseases caused by excessive cell division.

The cancer includes all cancers capable of exhibiting prophylactic or therapeutic efficacy due to inhibition of PLK1 activity, and may be solid cancer or blood cancer. For example, the cancer may be one or more selected from the group consisting of squamous cell carcinoma, small cell lung cancer, non-small cell lung cancer, lung adenocarcinoma, lung squamous cell carcinoma, peritoneal cancer, skin cancer, skin or intraocular melanoma, rectal cancer, anal muscle cancer, esophageal cancer, small intestine cancer, endocrine cancer, parathyroid cancer, adrenal cancer, soft tissue sarcoma, urethral cancer, chronic or acute leukemia, lymphocytic lymphoma, hepatocellular carcinoma, gastrointestinal cancer, gastric cancer, pancreatic cancer, glioblastoma, cervical cancer, ovarian cancer, liver cancer, bladder cancer, liver tumor, breast cancer, colon cancer, colorectal cancer, endometrial or uterine cancer, salivary gland cancer, kidney cancer, prostate cancer, vulvar cancer, thyroid cancer, head and neck cancer, brain cancer, osteosarcoma, and the like, but is not limited thereto. The cancer includes not only primary cancer but also metastatic cancer.

The benign tumors include all benign tumors capable of exhibiting prophylactic or therapeutic efficacy due to the inhibition of PLK1 activity, such as benign tumors in pre-cancer stages, and may be solid tumors or blood tumors. For example, the tumor may be one or more selected from the group consisting of Barrett's esophagus, colon adenoma and polyp, breast fibroadenoma and cyst, monoclonal gammopathy of undetermined significance (MGUS), monoclonal lymphocytosis, and the like, but is not limited thereto.

The neurological diseases include all neurological diseases capable of exhibiting prophylactic or therapeutic efficacy due to the inhibition of PLK1 activity, and specifically, may be one or more selected from the group consisting of central nervous system disease, neurodegenerative disease, Alzheimer's disease, Parkinson's disease, multiple sclerosis, Huntington's disease, senile dementia, epilepsy, Lou Gehrig, stroke, and nerve damage and axonal degeneration-related disorders following brain or spinal cord injury, but is not limited thereto.

The pharmaceutical composition of the present invention may further include one or more active ingredients exhibiting the same or similar medicinal effects in addition to the compound represented by Formula I above, or the pharmaceutically acceptable salt thereof.

An embodiment of the present invention is a method of degrading PLK1 by administering a compound represented by Formula I or a pharmaceutically acceptable salt thereof to mammals including humans.

Another embodiment of the present invention is a method of degrading PLK1 by administering the compound represented by Formula I or the pharmaceutically acceptable salt thereof to a sample in vitro. The sample may be a cell, a cell culture, a body fluid or tissue of a mammal including a human, but is not limited thereto.

Advantageous Effects of Invention

The compound of the present invention exhibits an effect of inducing PLK1 degradation. Therefore, the pharmaceutical compound of the present invention may be effectively utilized for preventing or treating PLK1-related diseases.

BEST MODE FOR CARRYING OUT THE INVENTION

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

The present invention provides synthetic methods for Compound 1 to 6 shown in the table below.

TABLE 1

| Compound | Structure |
|---|---|
| 1 | 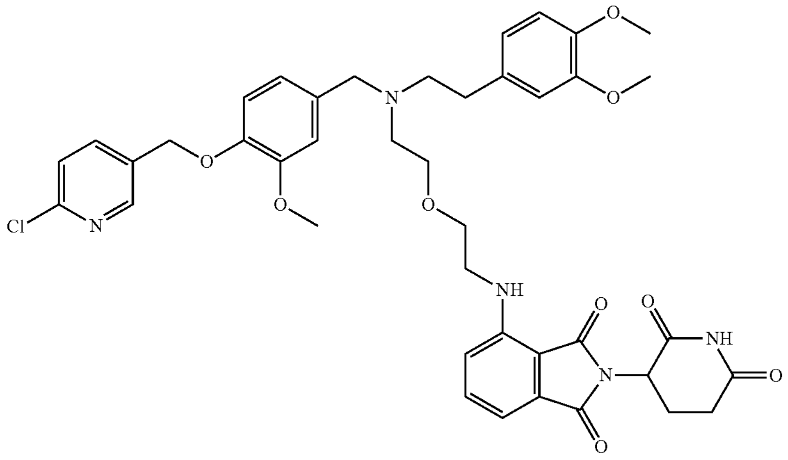 [SMILES: COc1ccc(CCN(CCOCCNc2cccc3c2C(=O)N(C2CCC(=O)NC2=O)C3=O)Cc2ccc(OCc3ccc(Cl)nc3)c(OC)c2)cc1OC] |
| 2 | 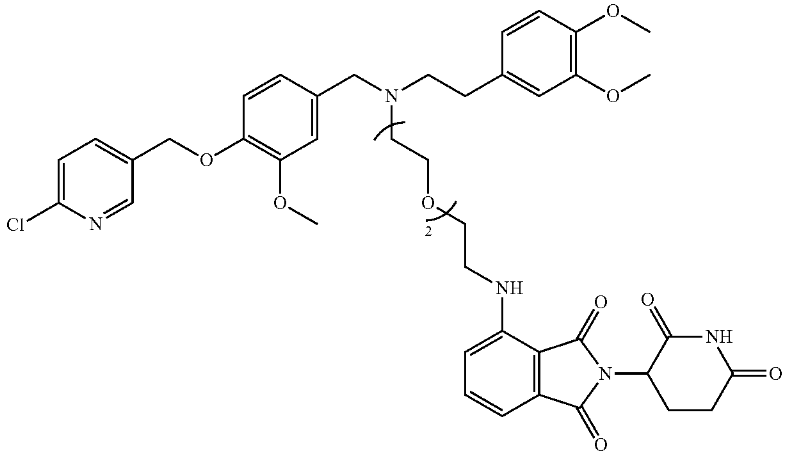 |

TABLE 1-continued
| Compound | Structure |
| --- | --- |
| 3 | 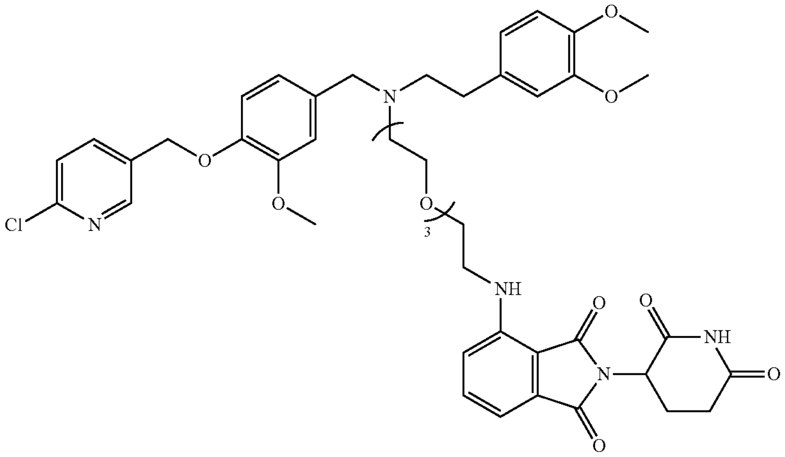 |
| 4 | 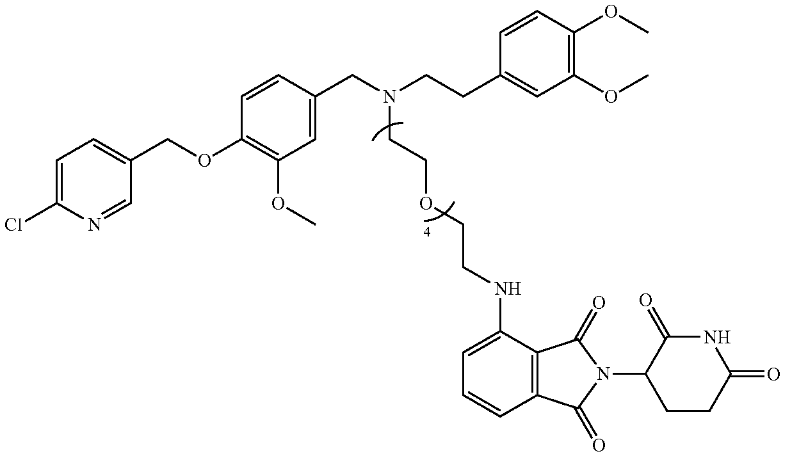 |
| 5 | 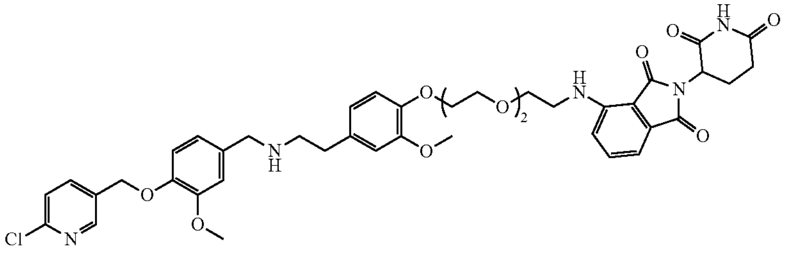 |

TABLE 1-continued

| Compound | Structure |
|---|---|
| 6 | 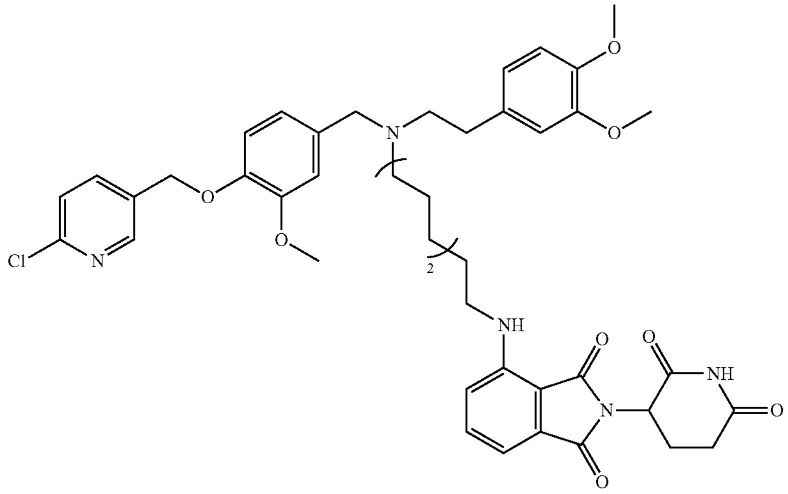 |

The compounds of the present invention were purified according to the following method and the structure was analyzed.

Instruments

LCMS: Shimadzu LCMS-2020

NMR: BRUKER AVANCE III/400 MHz

HPLC: Shimadzu LC-20AB, Shimadzu LC-20AD, Agilent 1100 LC, Agilent 1200 LC, Agilent 1290 LC LCSM Analysis LCMS data were recorded with Shimadzu LCMS-2020 equipped with an electron spray ionization device. 0.0375% TFA in water (solvent A) and 0.01875% TFA in acetonitrile (solvent B) were used as mobile phases. As a column, Kinetex EVO C18 (2.1*30) mm, 5 um was used.

HPLC Analysis

In HPLC analysis, Shimadzu LC-20AB, Shimadzu LC-20AD, Agilent 1100 LC, Agilent 1200 LC or Agilent 1290 LC was used. 0.0375% TFA in water (solvent A) and 0.01875% TFA in acetonitrile (solvent B) or 0.025% $NH_3$·H2O in water (solvent A) and acetonitrile (Solvent B) was used as the mobile phase. As a column, XBridge C18 (2.1*50) mm, 5 um or Kinetex C18 LC column (4.6*50) mm, 5 um or Eclipse plus C18 (4.6*150) mm, 3.5 um or Waters XBridge® C18 (4.6*150) mm, 3.5 μm was used.

NMR Analysis $^1$H NMR spectrum was recorded with Bruker AVANCE III 400 MHz/5 mm Probe (BBO).

Example 1. Synthesis of 4-((2-(2-((4-((6-chloropyridin-3-yl)methoxy)-3-methoxybenzyl)(3,4-dimethoxyphenethyl)amino)ethoxy)ethyl)amino)-2-(2,6-dioxopiperidin-3-yl)isoindoline-1,3-dione (Compound 1)

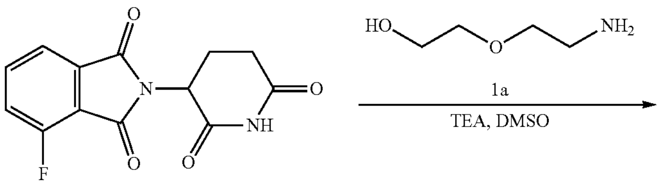

1

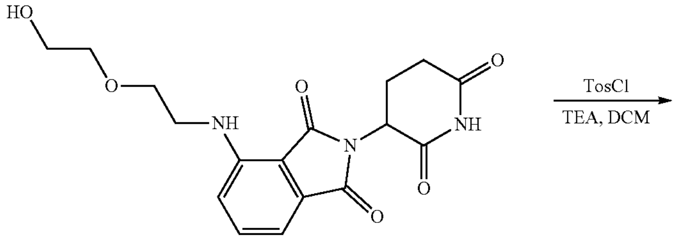

2

-continued

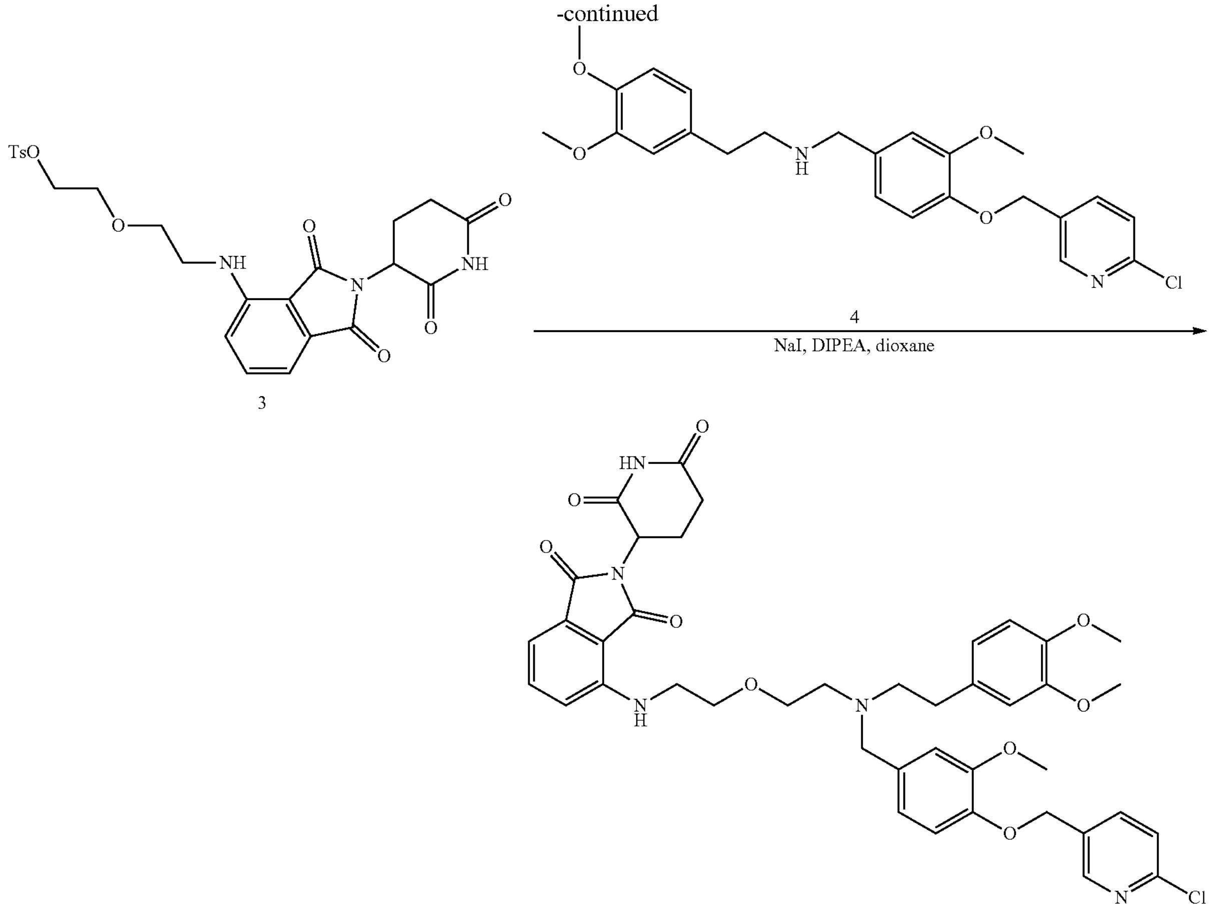

Compound 1

Step 1: Synthesis of 2-(2,6-dioxopiperidin-3-yl)-4-((2-(2-hydroxyethoxy)ethyl)amino)isoindoline-1,3-dione (2)

To a mixture of 2-(2,6-dioxopiperidin-3-yl)-4-fluoroisoindoline-1,3-dione (8 g, 28.96 mmol) in DMSO (50 mL) was added TEA (8.79 g, 86.89 mmol, 12.09 mL) and 2-(2-aminoethoxy)ethanol (3.96 g, 37.65 mmol, 3.77 mL) in one portion at 20° C. The mixture was stirred at 80° C. for 16 h. LC-MS showed reactant was consumed completely and one peak (70%) with desired mass. The reaction mixture was partitioned between $H_2O$ (300 mL) and EtOAc (600 mL). The organic phase was separated, washed with brine (100 mL×3), dried over $Na_2SO_4$, filtered and concentrated under reduced pressure. The residue was purified by column chromatography ($SiO_2$, Petroleum ether/Ethyl acetate=1/0 to 0/1) to afford 2-(2,6-dioxopiperidin-3-yl)-4-((2-(2-hydroxyethoxy)ethyl)amino)isoindoline-1,3-dione (10.4 g, 27.92 mmol, 96.39% yield, 97% purity) as a green solid. $MS(M+H)^+=362.1$ Step 2: Synthesis of 2-(2-((2-(2,6-dioxopiperidin-3-yl)-1,3-dioxoisoindolin-4-yl)amino)ethoxy)ethyl 4-methylbenzenesulfonate (3)

To a solution of 2-(2,6-dioxopiperidin-3-yl)-4-((2-(2-hydroxyethoxy)ethyl)amino)isoindoline-1,3-dione (10.4 g, 28.78 mmol) in DCM (100 mL) were added TEA (4.37 g, 43.17 mmol, 6.01 mL) and TosCl (6.58 g, 34.54 mmol). The mixture was stirred at 20° C. for 16 hr. LCMS showed reactant was consumed completely and 100% of desired compound was detected. The mixture was concentrated under vacuum and the residue was purified by column chromatography ($SiO_2$, Petroleum ether/Ethyl acetate=1/0 to 1/3) afford 2-(2-((2-(2,6-dioxopiperidin-3-yl)-1,3-dioxoisoindolin-4-yl)amino)ethoxy)ethyl 4-methylbenzenesulfonate (4.65 g, 8.57 mmol, 29.77% yield, 95% purity)) as a yellow solid. MS $(M+H)^+=516.1$ Step 3: Synthesis of 4-((2-(2-((4-((6-chloropyridin-3-yl)methoxy)-3-methoxybenzyl) (3,4-dimethoxyphenethyl)amino)ethoxy)ethyl)amino)-2-(2,6-dioxopiperidin-3-yl)isoindoline-1,3-dione (Compound 1)

To a solution of 2-(2-((2-(2,6-dioxopiperidin-3-yl)-1,3-dioxoisoindolin-4-yl)amino)ethoxy)ethyl 4-methylbenzenesulfonate (200 mg, 451.53 μmol) and 2-(2-((2-(2,6-dioxopiperidin-3-yl)-1,3-dioxoisoindolin-4-yl)amino)ethoxy)ethyl 4-methylbenzenesulfonate (256.06 mg, 496.68 μmol) in dioxane (2 mL) were added DIPEA (175.07 mg, 1.35 mmol, 235.95 μL) and NaI (13.54 mg, 90.31 μmol, 0.2 eq) at 25° C. The reaction mixture was heated to 100° C. for 16 hours. LCMS showed the 2-[2-[[2-(2,6-dioxo-3-piperidyl)-1,3-dioxo-isoindolin-4-yl]amino]ethoxy]ethyl 4-methylbenzenesulfonate was consumed completely, and a main peak with desired mass. The mixture solution was concentrated under reduced pressure. The crude product was purified prep-HPLC (column: Phenomenex Gemini-NX $C_{18}$ 75*30 mm*3 um; mobile phase: [water (10 mM $NH_4HCO_3$)-ACN]; B %: 42%-72%, 8 min) and lyophilized to give 4-((2-(2-((4-((6-chloropyridin-3-yl)methoxy)-3-methoxybenzyl)(3,4-dimethoxyphenethyl)amino)ethoxy)ethyl)amino)-2-(2,6-dioxopiperidin-3-yl)isoindoline-1,3-dione (188.4 mg, 232.42 μmol, 51.47% yield, 97% purity) as yellow solid. MS(M+H)+=786.2

$^1$H NMR (400 MHz, $CDCl_3$) δ=8.45 (d, J=2.0 Hz, 1H), 8.09 (br s, 1H), 7.78 (dd, J=2.4, 8.2 Hz, 1H), 7.48 (dd, J=7.2, 8.3 Hz, 1H), 7.34 (d, J=8.0 Hz, 1H), 7.10 (d, J=6.8 Hz, 1H), 6.90 (d, J=8.4 Hz, 2H), 6.82-6.71 (m, 3H), 6.70-6.61 (m, 2H), 6.48 (br t, J=5.6 Hz, 1H), 5.10 (s, 2H), 4.93-4.82 (m, 1H), 3.84-3.80 (m, 9H), 3.69-3.52 (m, 6H), 3.47-3.39 (m, 2H), 2.90-2.68 (m, 9H), 2.13-2.03 (m, 1H).

Example 2. Synthesis of 4-((2-(2-(2-((4-((6-chloropyridin-3-yl)methoxy)-3-methoxybenzyl)(3,4-dimethoxyphenethyl)amino)ethoxy)ethoxy)ethyl)amino)-2-(2,6-dioxopiperidin-3-yl)isoindoline-1,3-dione (Compound 2)

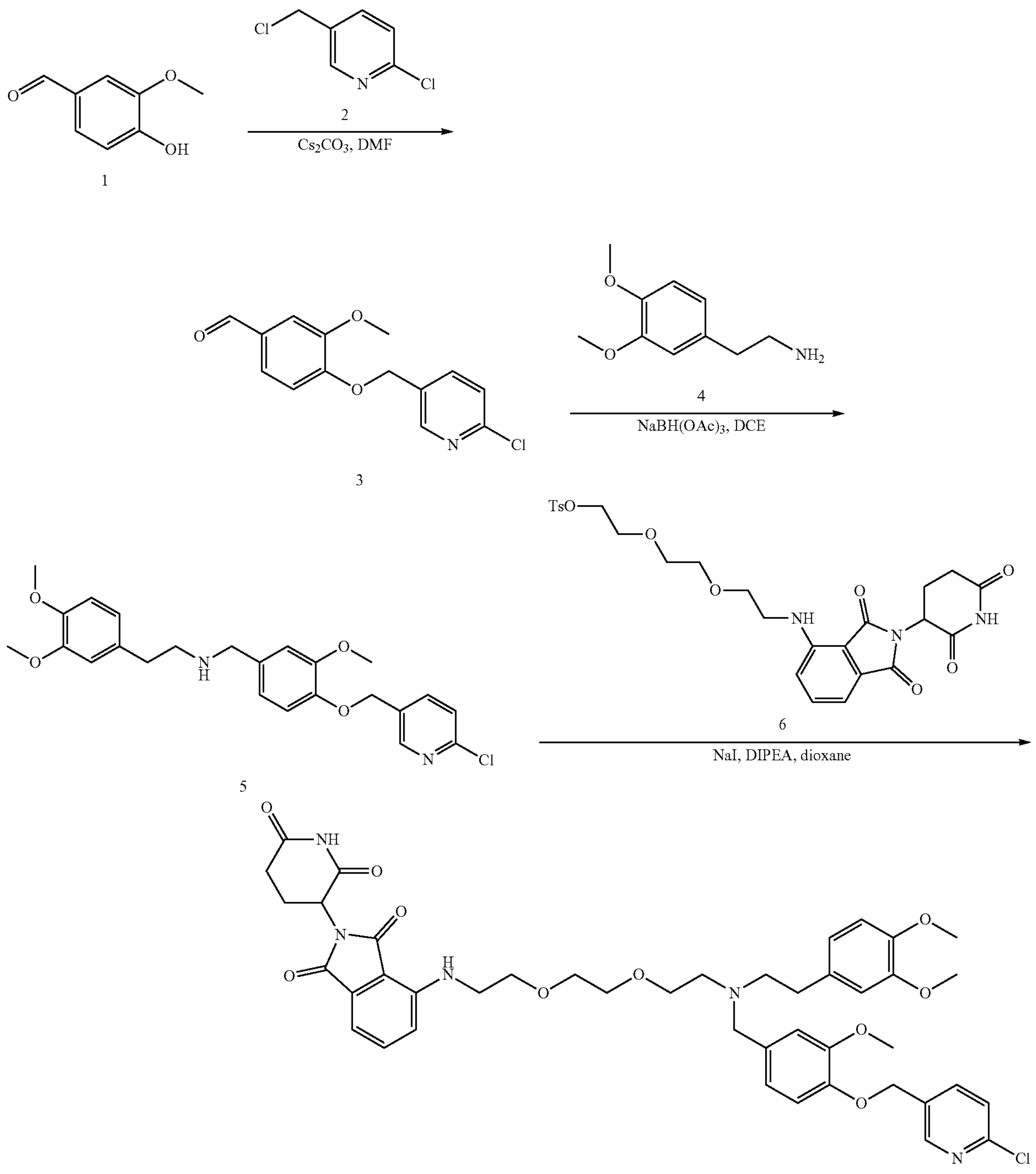

1
2
3
4
5
6

Compound 2

-continued

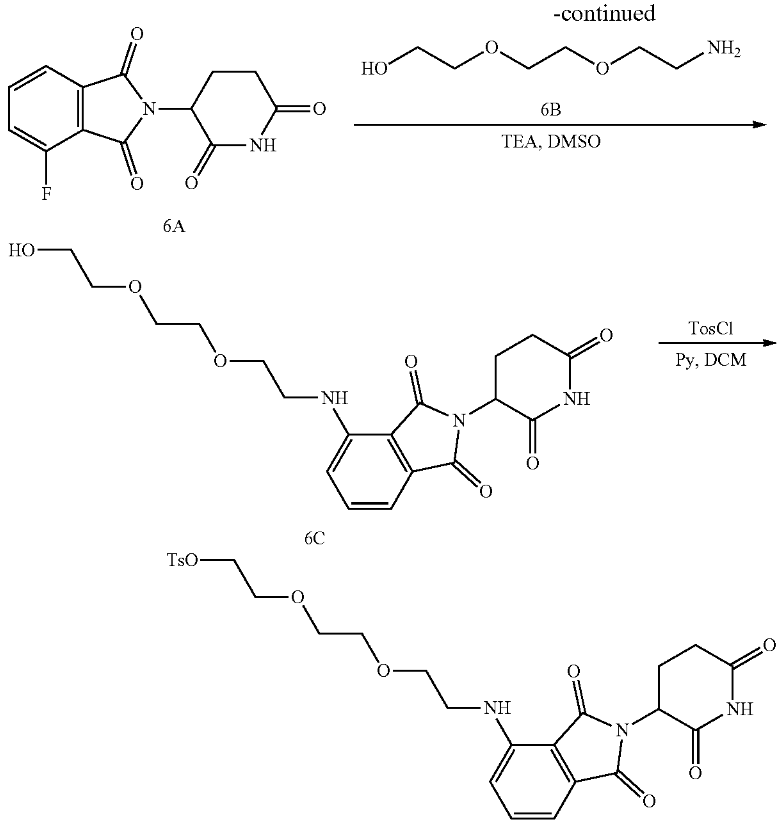

6A

6C

6

Step 1: Synthesis of 2-(2,6-dioxopiperidin-3-yl)-4-((2-(2-(2-hydroxyethoxy)ethoxy)ethyl)amino)isoindoline-1,3-dione (6C)

To a solution of 2-(2,6-dioxopiperidin-3-yl)-4-fluoroisoindoline-1,3-dione (7 g, 25.34 mmol) and 2-(2-(2-aminoethoxy)ethoxy)ethanol (3.78 g, 25.34 mmol) in DMSO (80 mL) was added TEA (5.13 g, 50.68 mmol, 7.05 mL). The mixture was heated to 90° C. for 16 hr. LCMS showed one peak (48%) with desired mass. The reaction mixture was diluted with $H_2O$ (400 mL) and extracted with EtOAc (400 mL×5). The combined organic layer was dried over $Na_2SO_4$, filtered and concentrated in vacuo to afford 2-(2,6-dioxopiperidin-3-yl)-4-((2-(2-(2-hydroxyethoxy)ethoxy)ethyl)amino)isoindoline-1,3-dione (6.1 g, 15.05 mmol, 59.37% yield)) as a green oil. MS(M+H)$^+$=406.0

Step 2: Synthesis of 2-(2-(2-((2-(2,6-dioxopiperidin-3-yl)-1,3-dioxoisoindolin-4-yl)amino)ethoxy)ethoxy)ethyl 4-methylbenzenesulfonate (6)

To a solution of 2-(2,6-dioxopiperidin-3-yl)-4-((2-(2-(2-hydroxyethoxy)ethoxy)ethyl)amino)isoindoline-1,3-dione (5.1 g, 12.58 mmol) in DCM (60 mL) were added TosCl (11.99 g, 62.90 mmol) and Py (7.96 g, 100.64 mmol, 8.12 mL). The mixture was stirred at 15° C. for 16 hr. LCMS showed one peak (72%) with desired mass. The mixture was combined another batch (1 g scale). The combined mixture was diluted with $H_2O$ (100 mL) and extracted with DCM (200 mL×2). The combined organic layer was dried over $Na_2SO_4$, filtered. The filtrate was concentrated in vacuo. The residue was purified by column chromatography ($SiO_2$, PE/EtOAc: 30%-80%) to afford 2-(2-(2-((2-(2,6-dioxopiperidin-3-yl)-1,3-dioxoisoindolin-4-yl)amino)ethoxy)ethoxy)ethyl 4-methylbenzenesulfonate (7.2 g, 10.42 mmol, 82.84% yield, 81% purity) a green oil.

MS(M+H)$^+$=560.2.

Step 3: Synthesis of 4-[(6-chloro-3-pyridyl)methoxy]-3-methoxy-benzaldehyde (3)

A mixture of 4-hydroxy-3-methoxy-benzaldehyde (10 g, 65.73 mmol), 2-chloro-5-(chloromethyl)pyridine (11.71 g, 72.30 mmol) and $Cs_2CO_3$ (27.84 g, 85.44 mmol) in DMF (200 mL) was stirred at 70° C. for 2 hours. LCMS showed reactant was consumed completely and 91% of desired mass was detected. The reaction mixture was diluted with $H_2O$ (300 mL) and extracted with EtOAc (500 mL×3). The combined organic layers were washed with brine (800 mL×3), dried over $Na_2SO_4$, filtered and concentrated under reduced pressure. The residue was triturated with Petroleum ether/Ethyl acetate=20/1 and filtered. The filtrate was concentrated under reduced pressure to afford 4-[(6-chloro-3-pyridyl) methoxy]-3-methoxy-benzaldehyde (18 g, 64.82 mmol, 98.62% yield) as a brown solid.

MS(M+H)$^+$=278.1.

H NMR: $^1$H NMR (400 MHz, DMSO-$d_6$) δ=9.85 (s, 1H), 8.53 (d, J=2.0 Hz, 1H), 7.95 (dd, $J_1$=8.2 Hz, $J_2$=2.4 Hz, 1H), 7.61-7.51 (m, 2H), 7.43 (d, J=1.9 Hz, 1H), 7.29 (d, J=8.3 Hz, 1H), 5.27 (s, 2H), 3.84 (s, 3H).

Step 4: Synthesis of N-(4-((6-chloropyridin-3-yl)methoxy)-3-methoxybenzyl)-2-(3,4-dimethoxyphenyl)ethanamine (5)

A mixture of 4-((6-chloropyridin-3-yl)methoxy)-3-methoxybenzaldehyde (4 g, 14.40 mmol) and 2-(3,4-dimethoxyphenyl)ethanamine (2.87 g, 15.84 mmol, 2.63 mL) in DCE (70 mL) was stirred at 15° C. for 3 hours, then $NaBH(OAc)_3$ (3.51 g, 16.56 mmol) was added and the resulting mixture was stirred at 15° C. for 16 hours. LCMS showed reagent was consumed completely and 65% of desired mass was detected. The mixture was concentrated under reduced pressure. The residue was diluted with $NaHCO_3$ solution (80 mL) and extracted with ethyl acetate (100 mL×3). The combined organic layer was dried over $Na_2SO_4$, filtered and concentrated under reduced pressure. The residue was purified by flash silica gel chromatography (25 g SepaFlash® Silica Flash Column, Eluent of 0~14% MeOH/Ethyl acetate@ 65 mL/min) to afford N-(4-((6-chloropyridin-3-yl)methoxy)-3-methoxybenzyl)-2-(3,4-dimethoxyphenyl)ethanamine (3.6 g, 7.88 mmol, 54.73% yield, 97% purity)) as a off-white gum. MS$(M+H)^+$=443.2.

Step 5: Synthesis of 4-((2-(2-(2-((4-((6-chloropyridin-3-yl)methoxy)-3-methoxybenzyl)(3,4-dimethoxyphenethyl)amino)ethoxy)ethoxy)ethyl)amino)-2-(2,6-dioxopiperidin-3-yl)isoindoline-1,3-dione (Compound 2)

To a solution of N-(4-((6-chloropyridin-3-yl)methoxy)-3-methoxybenzyl)-2-(3,4-dimethoxyphenyl)ethanamine (200 mg, 451.53 μmol) and 2-(2-(2-((2-(2,6-dioxopiperidin-3-yl)-1,3-dioxoisoindolin-4-yl)amino)ethoxy)ethoxy)ethyl 4-methylbenzenesulfonate (277.94 mg, 496.69 μmol) in 1,4-dioxane (4 mL) were added DIEA (175.07 mg, 1.35 mmol, 235.95 μL) and NaI (13.54 mg, 90.31 μmol). The reaction mixture was heated to 100° C. for 16 hours. LCMS showed 11% of reactant remained and 48% of desired mass was detected. The reaction mixture was concentrated under reduced pressure. The residue was purified by prep-HPLC (column: Waters Xbridge $C_{18}$ 150*50 mm*10 um; mobile phase: [water (10 mM $NH_4HCO_3$)-ACN]; B %: 43%-73%, 11.5 min) to afford 4-((2-(2-(2-((4-((6-chloropyridin-3-yl)methoxy)-3-methoxybenzyl)(3,4-dimethoxyphenethyl)amino)ethoxy)ethoxy)ethyl)amino)-2-(2,6-dioxopiperidin-3-yl)isoindoline-1,3-dione (210 mg, 237.74 μmol, 52.65% yield, 94% purity)) as yellow solid. MS$(M+H)^+$=830.4

$^1$H NMR (400 MHz, DMSO-$d_6$) δ=11.09 (s, 1H), 8.47 (d, J=2.1 Hz, 1H), 7.90 (dd, J=2.4, 8.2 Hz, 1H), 7.59-7.50 (m, 2H), 7.10 (d, J=8.6 Hz, 1H), 7.02 (d, J=7.0 Hz, 1H), 6.93 (d, J=8.2 Hz, 1H), 6.87 (d, J=1.7 Hz, 1H), 6.81-6.71 (m, 3H), 6.64 (dd, J=1.8, 8.1 Hz, 1H), 6.58 (t, J=5.7 Hz, 1H), 5.08 (s, 2H), 5.03 (dd, J=5.4, 12.9 Hz, 1H), 3.69 (d, J=2.4 Hz, 9H), 3.62-3.51 (m, 6H), 3.51-3.38 (m, 7H), 2.92-2.79 (m, 1H), 2.69-2.56 (m, 7H), 2.04-1.92 (m, 1H)

Example 3: Synthesis of 4-((3-(4-((6-chloropyridin-3-yl)methoxy)-3-methoxybenzyl)-1-(3,4-dimethoxyphenyl)-6,9,12-trioxa-3-azatetradecan-14-yl)amino)-2-(2,6-dioxopiperidin-3-yl)isoindoline-1,3-dione (Compound 3)

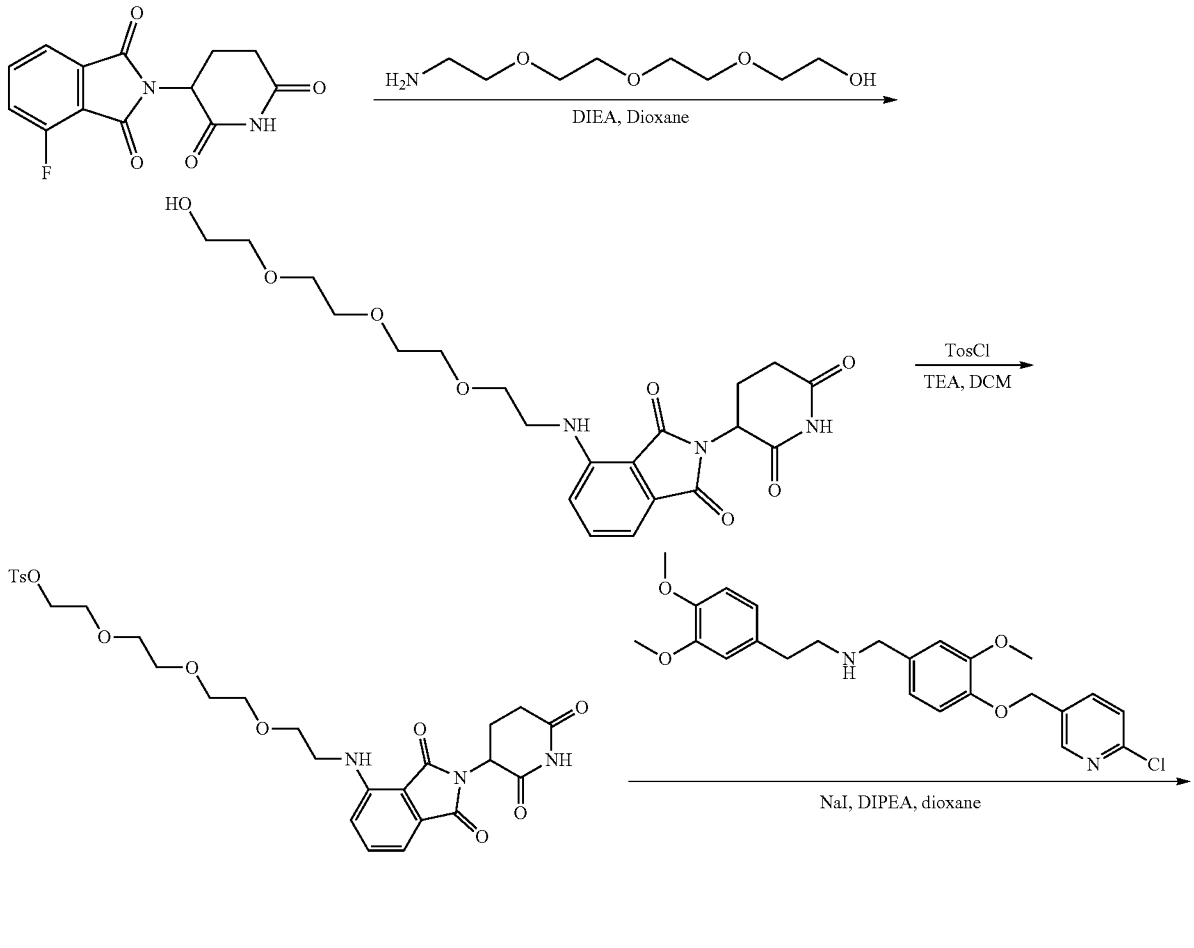

-continued

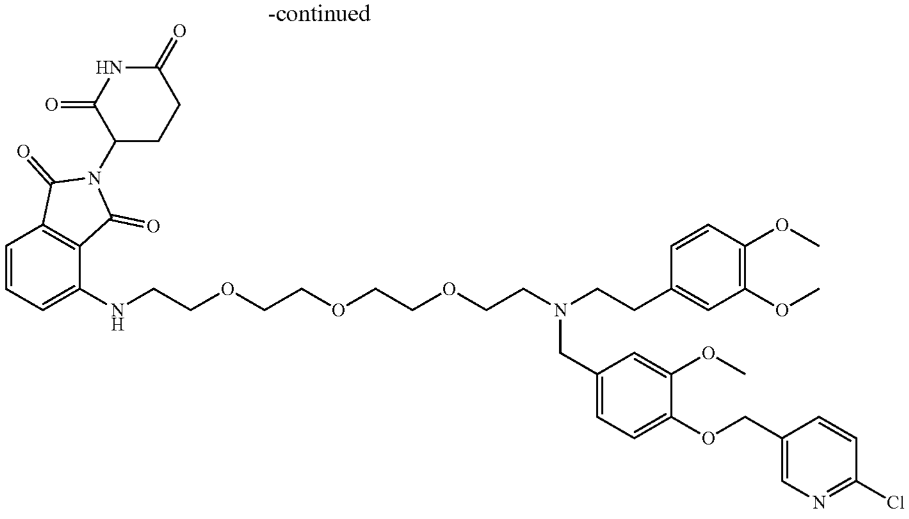

Compound 3

Referring to the above reaction scheme, the titled compound (172.5 mg, 189.39 μmol, 41.94% yield, 96% purity) was obtained as yellow solid. MS(M+H)$^+$=874.2

$^1$H NMR (400 MHz, $CDCl_3$) δ=8.45 (d, J=2.4 Hz, 1H), 7.77 (dd, J=2.4, 8.2 Hz, 1H), 7.48 (dd, J=7.2, 8.3 Hz, 1H), 7.34 (d, J=8.4 Hz, 1H), 7.10 (d, J=7.2 Hz, 1H), 6.94-6.86 (m, 2H), 6.82-6.73 (m, 3H), 6.71-6.63 (m, 2H), 6.48 (t, J=5.6 Hz, 1H), 5.10 (s, 2H), 4.93-4.86 (m, 1H), 3.87-3.81 (m, 9H), 3.72-3.67 (m, 2H), 3.67-3.61 (m, 8H), 3.60-3.52 (m, 4H), 3.45-3.40 (m, 2H), 2.91-2.83 (m, 1H), 2.82-2.67 (m, 8H), 2.19-2.05 (m, 1H).

Example 4: Synthesis of 4-((3-((6-chloropyridin-3-yl)methoxy)-3-methoxybenzyl)-1-(3,4-dimethoxyphenyl)-6,9,12,15-tetraoxa-3-azaheptadecan-17-yl)amino)-2-(2,6-dioxopiperidin-3-yl)isoindoline-1,3-dione (Compound 4)

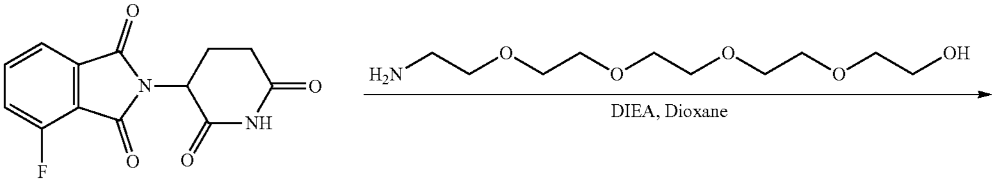

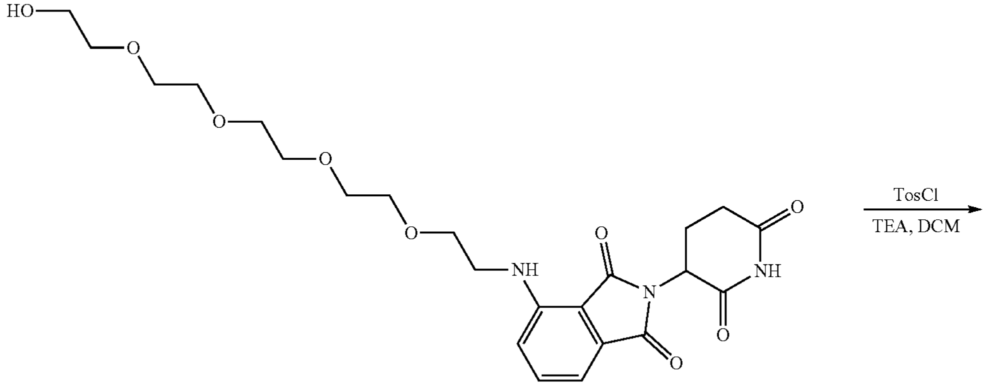

-continued

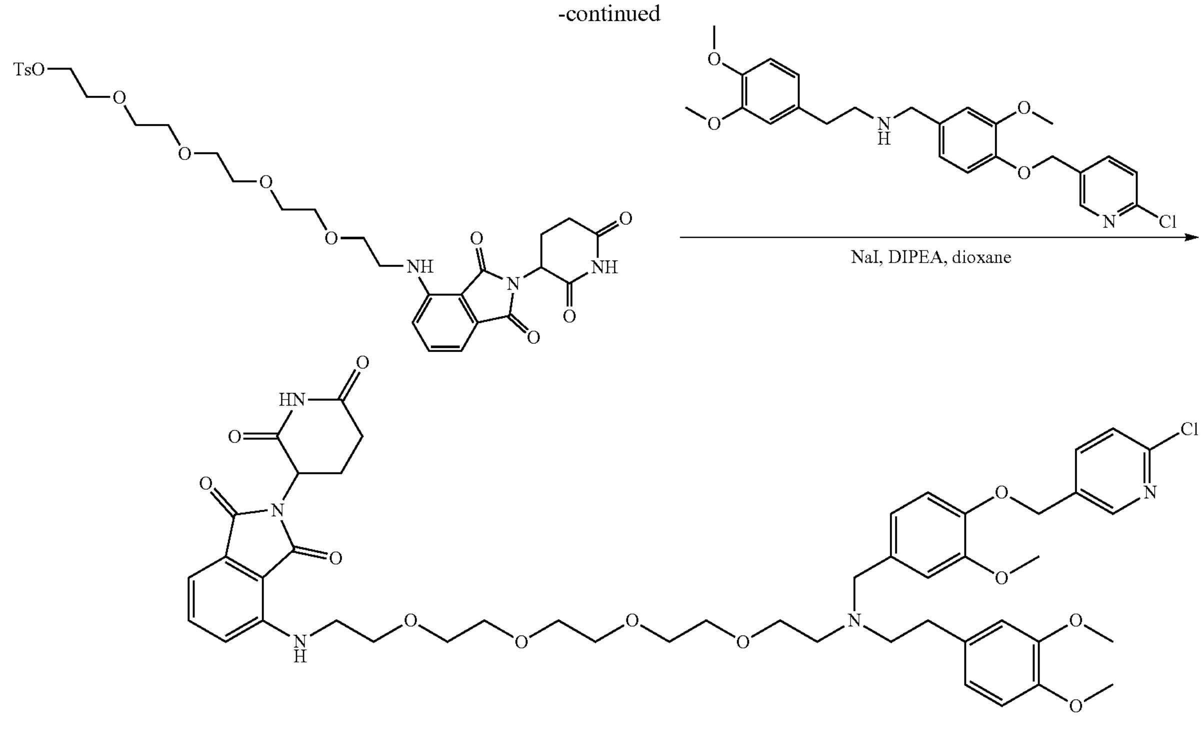

Compound 4

Referring to the above reaction scheme, the titled compound (63.1 mg, 63.90 μmol, 14.15% yield, 93% purity) as yellow solid. MS$(M+H)^+$=918.2

$^1$H NMR (400 MHz, DMSO-$d_6$) δ=11.09 (br s, 1H), 8.47 (d, J=2.0 Hz, 1H), 7.90 (dd, J=2.4, 8.2 Hz, 1H), 7.60-7.51 (m, 2H), 7.12 (d, J=8.6 Hz, 1H), 7.03 (d, J=7.0 Hz, 1H), 6.94 (d, J=8.0 Hz, 1H), 6.88 (d, J=1.6 Hz, 1H), 6.83-6.72 (m, 3H), 6.68-6.62 (m, 1H), 6.59 (t, J=5.6 Hz, 1H), 5.13-4.99 (m, 3H), 3.73-3.65 (m, 9H), 3.63-3.55 (m, 4H), 3.55-3.40 (m, 16H), 2.94-2.81 (m, 1H), 2.72-2.52 (m, 8H), 2.06-1.94 (m, 1H)

Example 5: Synthesis of 4-((2-(2-(2-(4-(2-((4-((6-chloropyridin-3-yl)methoxy)-3-methoxybenzyl)amino)ethyl)-2-methoxyphenoxy)ethoxy)ethoxy)ethyl)amino)-2-(2,6-dioxopiperidin-3-yl)isoindoline-1,3-dione (Compound 5)

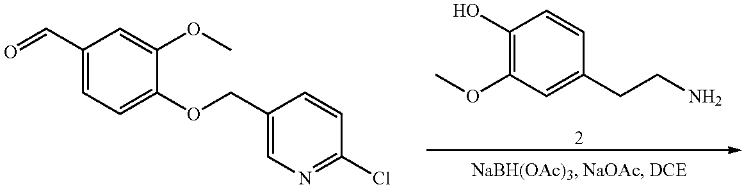

1

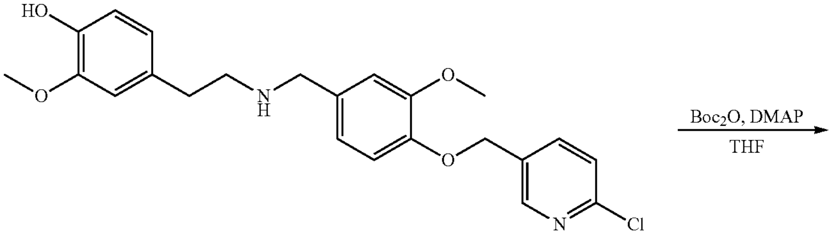

3

-continued

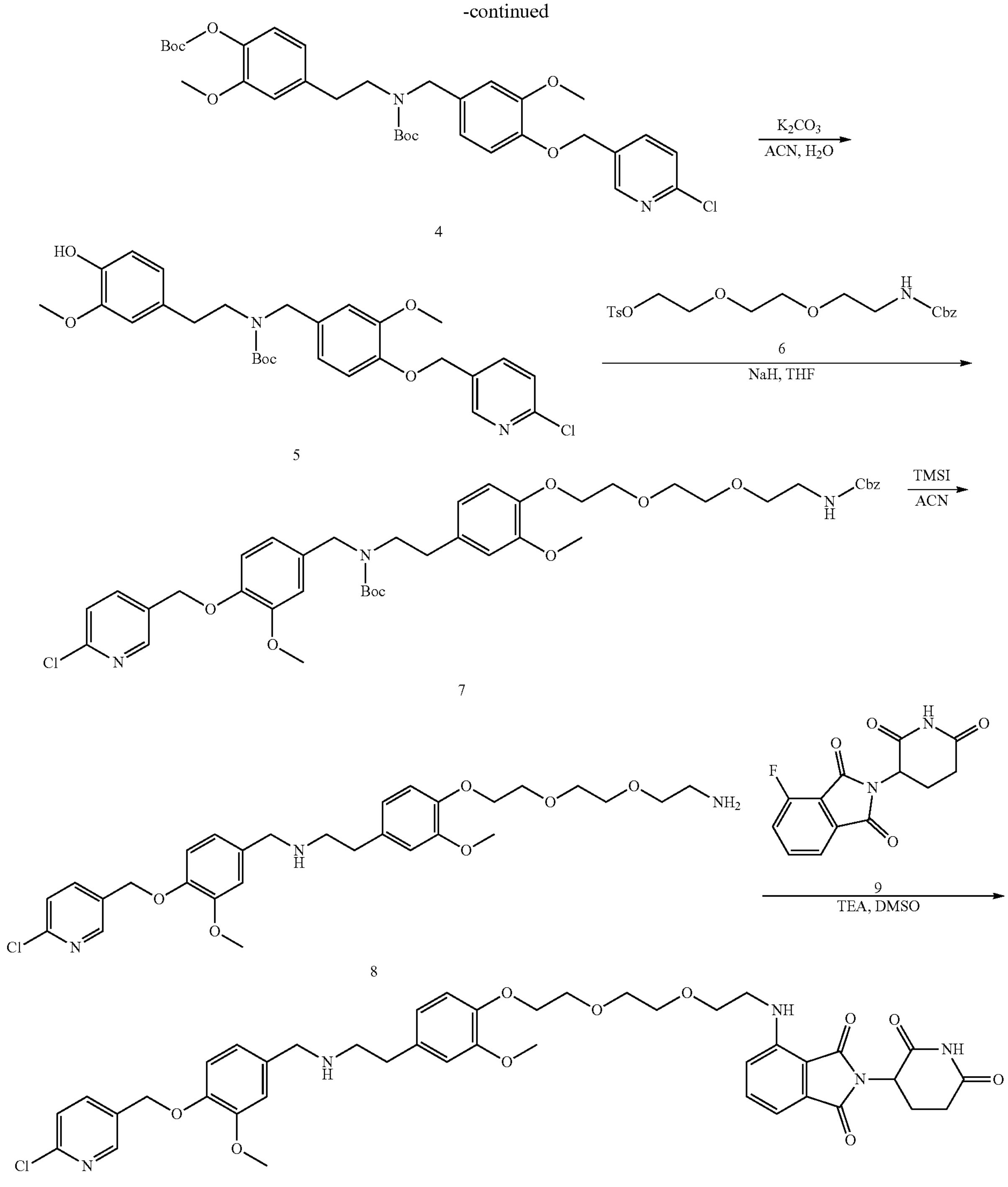

4

5

7

8

Compound 5

Step 1: Synthesis of 4-(2-((4-((6-chloropyridin-3-yl) methoxy)-3-methoxybenzyl)amino)ethyl)-2-methoxyphenol (3)

To a solution of 4-((6-chloropyridin-3-yl)methoxy)-3-methoxybenzaldehyde (2 g, 7.20 mmol) and 4-(2-aminoethyl)-2-methoxyphenol (1.76 g, 8.64 mmol, HCl salt) in DCE (50 mL) was added NaOAc (709 mg, 8.64 mmol) and the mixture was stirred at 25° C. for 0.5 h. Then NaBH$(OAc)_3$ (4.58 g, 21.61 mmol) was added and the resulting mixture was stirred at 25° C. for 14 h. LCMS showed the desired mass was detected. The mixture was diluted with $H_2O$ (30 mL) and filtered. The filter cake was washed with $H_2O$ (30 mL). The filter cake was diluted with $H_2O$ (20 mL) and EtOAc (20 mL), the suspension was adjusted the pH=8 with saturated $Na_2CO_3$ solution and extracted with EtOAc (10 mL×3). The combined organic layer was washed with $H_2O$ (10 mL), dried over $Na_2SO_4$ and filtered. The filtrate was concentrated under reduced pressure to afford 4-(2-((4-((6-chloropyridin-3-yl)methoxy)-3-methoxybenzyl)amino)ethyl)-2-methoxyphenol (1.7 g, crude) as yellow oil. MS$(M+H)^+$=429.3

Step 2: Synthesis of [4-[2-[tert-butoxycarbonyl-[[4-[(6-chloro-3-pyridyl)methoxy]-3-methoxy-phenyl]methyl]amino]ethyl]-2-methoxy-phenyl]tert-butyl carbonate (4)

To a solution of 4-(2-((4-((6-chloropyridin-3-yl)methoxy)-3-methoxybenzyl)amino)ethyl)-2-methoxyphenol (1.7 g, 3.96 mmol) in THF (40 mL) was added DMAP (24.21 mg, 198.18 μmol) and $Boc_2O$ (2.60 g, 11.89 mmol, 2.73 mL) and the mixture was stirred at 25° C. for 14 h. LCMS showed the desired mass was detected. The mixture was concentrated under reduced pressure and purified by flash silica gel chromatography (20 g SepaFlash® Silica Flash Column, Eluent of 0~40% Ethyl acetate/Petroleum ether gradient @ 50 mL/min) to afford [4-[2-[tert-butoxycarbonyl-[[4-[(6-chloro-3-pyridyl)methoxy]-3-methoxy-phenyl]meth yl]amino]ethyl]-2-methoxy-phenyl]tert-butyl carbonate (1.7 g, 2.70 mmol, 68.17% yield, 100% purity) as yellow oil. MS$(M+H)^+$=629.5

Step 3: Synthesis of tert-butyl N-[[4-[(6-chloro-3-pyridyl)methoxy]-3-methoxy-phenyl]methyl]-N-[2-(4-hydroxy-3-methoxy-phenyl)ethyl]carbamate (5)

To a solution of [4-[2-[tert-butoxycarbonyl-[[4-[(6-chloro-3-pyridyl)methoxy]-3-methoxy-phenyl]meth yl]amino]ethyl]-2-methoxy-phenyl]tert-butyl carbonate (1.7 g, 2.70 mmol) in ACN (15 mL) and $H_2O$ (7.5 mL) was added $K_2CO_3$ (746.89 mg, 5.40 mmol) and the mixture was stirred at 80° C. for 20 h. LCMS showed the desired mass was detected. The mixture was extracted with EtOAc (10 mL×3), the combined organic layer was washed with $H_2O$ (20 mL), dried over $Na_2SO_4$ and filtered. The filtrate was concentrated under reduced pressure. The residue was purified by flash silica gel chromatography (12 g SepaFlash® Silica Flash Column, Eluent of 0-30% Ethyl acetate/Petroleum ether gradient @ 50 mL/min) to afford tert-butyl N-[[4-[(6-chloro-3-pyridyl)methoxy]-3-methoxy-phenyl]methyl]-N-[2-(4-hydroxy-3-methoxy-phenyl)ethyl] carbamate (0.5 g, 945.14 μmol, 34.98% yield) as yellow oil. MS$(M+H)^+$=529.2

Step 4: Synthesis of tert-butyl N-[2-[4-[2-[2-[2 (benzyloxycarbonylamino)ethoxy]ethoxy]ethoxy]-3-methoxy-phenyl]ethyl]-N-[[4-[(6-chloro-3-pyridyl)methoxy]-3-methoxy-phenyl]methyl]carbamate (7)

To a solution of tert-butyl N-[[4-[(6-chloro-3-pyridyl)methoxy]-3-methoxy-phenyl]methyl]-N-[2-(4-hydroxy-3-methoxy-phenyl)ethyl]carbamate (450 mg, 850.62 μmol) in THF (9 mL) was added NaH (45.00 mg, 1.13 mmol, 60% purity) at 25° C. and the mixture was stirred at 25° C. for 0.5 h. Then 3-oxo-1-phenyl-2,7,10-trioxa-4-azadodecan-12-yl 4-methylbenzenesulfonate (484 mg, 1.11 mmol) in THF (3 mL) was added and the mixture was stirred at 50° C. for 28 h. LCMS showed the starting material remained, additional NaH (37 mg, 925.00 μmol, 60% purity) was added at 25° C. followed by a solution of 3-oxo-1-phenyl-2,7,10-trioxa-4-azadodecan-12-yl 4-methylbenzenesulfonate (372 mg, 850.27 μmol) in THF (2 mL) and the resulting mixture was stirred at 55° C. for 14 h. TLC (Petroleum ether:Ethyl acetate=1:1) showed new spot was detected. The mixture was quenched with $NH_4Cl$ (10 mL) and extracted with EtOAc (10 mL×3). The combined organic layer was washed with $H_2O$ (10 mL), dried over $Na_2SO_4$ and filtered. The filtrate was concentrated under reduced pressure. The residue was purified by column chromatography ($SiO_2$, Petroleum ether/Ethyl acetate=10/1 to 1/2) and re-purified by flash silica gel chromatography (12 g SepaFlash® Silica Flash Column, Eluent of 10-60% Ethyl acetate/Petroleum ether gradient @ 50 mL/min) to afford tert-butyl N-[2-[4-[2-[2-[2-(benzyloxycarbonylamino)ethoxy]ethoxy]ethoxy]-3-methoxy-phenyl]ethyl]-N-[[4-[(6-chloro-3-pyridyl)methoxy]-3-methoxy-phenyl]methyl]carbamate (0.7 g, crude) as yellow oil. MS$(M+H)^+$=794.6

Step 5: Synthesis of 2-(4-(2-(2-(2-aminoethoxy)ethoxy)ethoxy)-3-methoxyphenyl)-N-(4-((6-chloropyridin-3-yl)methoxy)-3-methoxybenzyl)ethanamine (8)

To a solution of tert-butyl N-[2-[4-[2-[2-[2-(benzyloxycarbonylamino)ethoxy]ethoxy]ethoxy]-3-methoxy-phenyl]ethyl]-N-[[4-[(6-chloro-3-pyridyl)methoxy]-3-methoxy-phenyl]methyl]carbamate (0.4 g, 503.57 μmol) in ACN (4 mL) was added TMSI (235.20 mg, 1.18 mmol, 160.00 μL) and the mixture was stirred at 25° C. for 2 h. LCMS showed major starting material remained. Additional TMSI (235.20 mg, 1.18 mmol, 160 μL) was added and the mixture was stirred at 25° C. for another 2 h. LCMS showed 23% of starting material remained. Additional TMSI (235.20 mg, 1.18 mmol, 160 μL) was added and the mixture was stirred at 25° C. for another 2 h. LCMS showed the starting material was consumed and 68% of the desired mass was detected. The mixture was concentrated under reduced pressure. The residue was purified by prep-HPLC (column: Phenomenex luna $C_{18}$ 150*40 mm*15 um; mobile phase: [water(0.1% TFA)-ACN]; B %: 9%-39%, 10 min) and the eluent was lyophilized to afford 2-(4-(2-(2-(2-aminoethoxy)ethoxy)ethoxy)-3-methoxyphenyl)-N-(4-((6-chloropyridin-3-yl)methoxy)-3-methoxybenzyl)ethanamine (360 mg, 399.05 μmol, 79.24% yield, 3TFA salt) as yellow oil. MS$(M+H)^+$=560.4

Step 6: Synthesis of 4-((2-(2-(2-(4-(2-((4-((6-chloropyridin-3-yl)methoxy)-3-methoxybenzyl)amino)ethyl)-2-methoxyphenoxy)ethoxy)ethoxy)ethyl)amino)-2-(2,6-dioxopiperidin-3-yl)isoindoline-1,3-dione (Compound 5)

To a solution of 2-(4-(2-(2-(2-aminoethoxy)ethoxy)ethoxy)-3-methoxyphenyl)-N-(4-((6-chloropyridin-3-yl)methoxy)-3-methoxybenzyl)ethanamine (210 mg, 232.78 μmol, 3TFA salt) and 2-(2,6-dioxopiperidin-3-yl)-4-fluoroisoindoline-1,3-dione (65.10 mg, 235.68 μmol) in DMSO (4 mL) was added TEA (152.67 mg, 1.51 mmol, 210.00 μL) and the mixture was stirred at 80° C. for 14 h. LCMS showed the desired mass was detected. The mixture was purified by prep-HPLC (column: Phenomenex Gemini-NX $C_{18}$ 75*30 mm*3 um; mobile phase: [water (10 mM $NH_4HCO_3$)-ACN]; B %: 32%-62%, 8 min) and the eluent was lyophilized. The crude was combined with another batch (250 mg scale) and purified by prep-HPLC (column: Phenomenex Synergi $C_{18}$ 150*25 mm*10 um; mobile phase: [water(0.1% TFA)-ACN]; B %: 27%-57%, 10 min) and the eluent was lyophilized to afford 4-((2-(2-(2-(4-(2-((4-((6-chloropyridin-3-yl)methoxy)-3-methoxybenzyl)amino)ethyl)-2-methoxyphenoxy)ethoxy)ethoxy)ethyl)amino)-2-

(2,6-dioxopiperidin-3-yl)isoindoline-1,3-dione (86.4 mg, 90.09 μmol, 38.70% yield, 97% purity, TFA salt) as yellow solid. MS$(M+H)^+$=816.4

$^1$H NMR (400 MHz, DMSO-$d_6$) δ=11.10 (s, 1H), 8.76 (br s, 1H), 8.49 (d, J=2.3 Hz, 1H), 7.96-7.88 (m, 1H), 7.61-7.53 (m, 2H), 7.18-7.10 (m, 3H), 7.05-6.98 (m, 2H), 6.89 (d, J=8.2 Hz, 1H), 6.83 (d, J=1.9 Hz, 1H), 6.74-6.69 (m, 1H), 6.64-6.58 (m, 1H), 5.18 (s, 2H), 5.08-5.02 (m, 1H), 4.11 (br t, J=5.5 Hz, 2H), 4.05-4.00 (m, 2H), 3.80 (s, 3H), 3.77-3.71 (m, 5H), 3.66-3.58 (m, 6H), 3.50-3.45 (m, 2H), 3.12 (br s, 2H), 2.92-2.82 (m, 3H), 2.62-2.53 (m, 2H), 2.09-1.94 (m, 1H).

Example 6: Synthesis of 4-((8-((4-((6-chloropyridin-3-yl)methoxy)-3-methoxybenzyl)(3,4-dimethoxyphenethyl)amino)octyl)amino)-2-(2,6-dioxopiperidin-3-yl)isoindoline-1,3-dione (Compound 6)

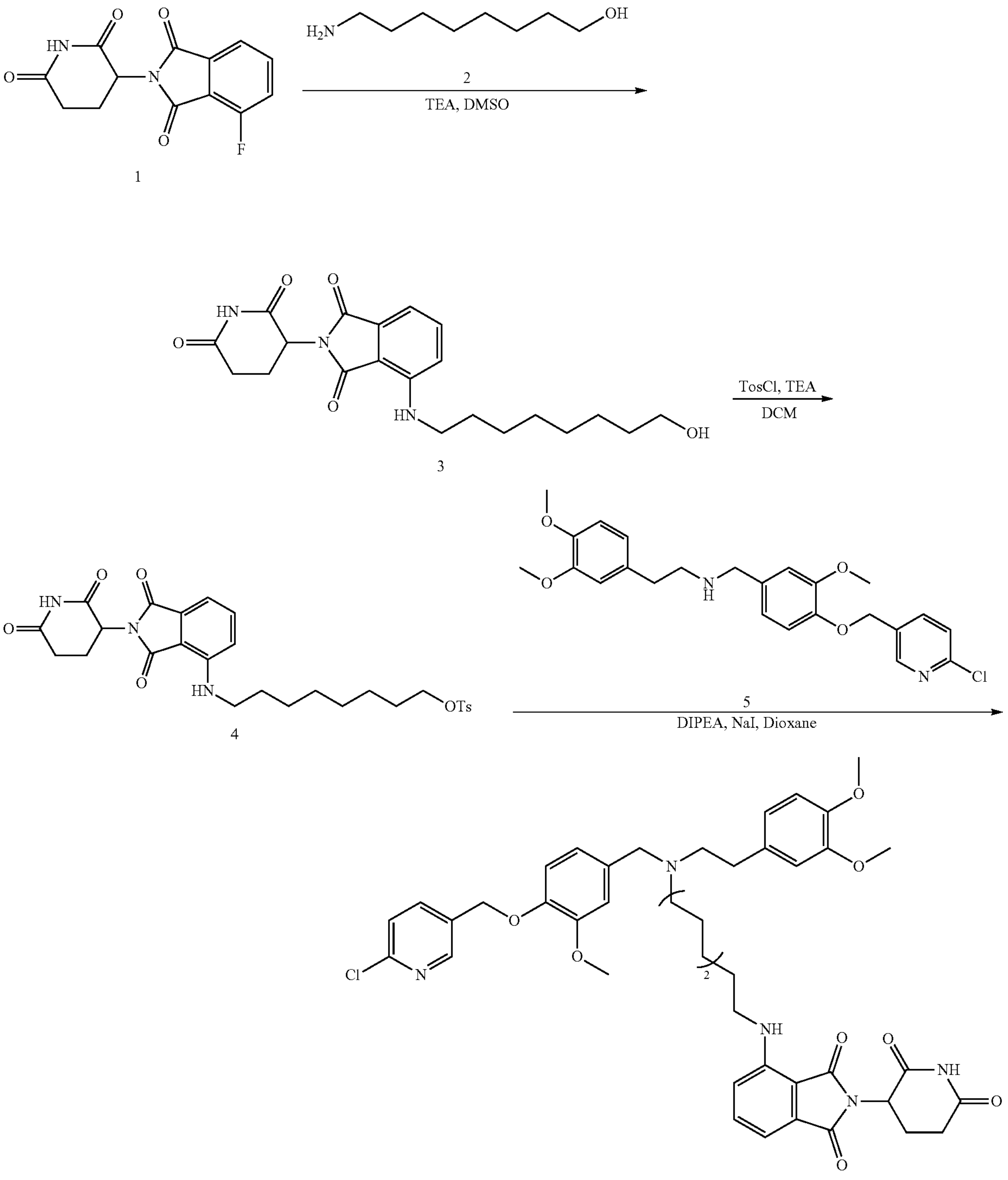

Compound 6

Step 1: Synthesis of 2-(2,6-dioxopiperidin-3-yl)-4-((8-hydroxyoctyl)amino)isoindoline-1,3-dione (3)

A solution of 2-(2,6-dioxopiperidin-3-yl)-4-fluoroisoindoline-1,3-dione (1.35 g, 4.89 mmol), 8-aminooctan-1-ol (851.83 mg, 5.86 mmol) and TEA (1.48 g, 14.66 mmol, 2.04 mL) in DMSO (20 mL) was stirred at 100° C. for 12 h. LCMS showed 8% peak with mass of 2-(2,6-dioxo-3-piperidyl)-4-fluoro-isoindoline-1,3-dione and a main peak with desired mass. The mixture was poured into water (100 mL) with ethyl acetate (50 mL×3). The combined organic phase was washed with brine (30 mL*3), dried over $Na_2SO_4$, filtered and concentrated under reduced pressure. The crude product was purified by silica gel column chromatography (1000 mesh silica gel, eluted with petroleum ether:ethyl acetate=10:1, 8:1, 5:1, 3:1, 1:1) afford 2-(2,6-dioxo-3-piperidyl)-4-(8-hydroxyoctylamino)isoindoline-1,3-dione (1.8 g, crude) as green oil which was used for the next step directly. $MS(M+H)^+$=402.1

Step 2: Synthesis of 8-((2-(2,6-dioxopiperidin-3-yl)-1,3-dioxoisoindolin-4-yl)amino)octyl 4-methylbenzenesulfonate (4)

To a solution 2-(2,6-dioxopiperidin-3-yl)-4-((8-hydroxyoctyl)amino)isoindoline-1,3-dione (1.8 g, 4.48 mmol), TEA (1.36 g, 13.45 mmol, 1.87 mL) in DCM (20 mL) was added TosCl (1.28 g, 6.73 mmol) at 25° C. The solution was stirred at 25° C. for 12 hr. LCMS showed the starting material was consumed completely and a main peak with desired mass. The mixture solution was concentrated under reduced pressure. The residue was purified by flash silica gel chromatography (25 g SepaFlash® Silica Flash Column, Eluent of 0~30% Ethyl acetate/Petroleum ether gradient @65 mL/min) to afford 8-((2-(2,6-dioxopiperidin-3-yl)-1,3-dioxoisoindolin-4-yl)amino)octyl 4-methylbenzenesulfonate (1.1 g, 1.94 mmol, 43.27% yield, 98% purity) as yellow oil. $MS(M+H)^+$=556.2

$^1$H NMR (400 MHz, DMSO-$d_6$) δ=11.09 (s, 1H), 7.77 (d, J=8.4 Hz, 2H), 7.57 (dd, J=7.2, 8.4 Hz, 1H), 7.47 (d, J=8.0 Hz, 2H), 7.13-6.97 (m, 2H), 6.53-6.48 (m, 1H), 5.09-5.01 (m, 1H), 4.00 (t, J=6.4 Hz, 2H), 3.31-3.20 (m, 2H), 2.95-2.80 (m, 1H), 2.68-2.51 (m, 2H), 2.40 (s, 3H), 2.08-1.99 (m, 1H), 1.58-1.46 (m, 4H), 1.32-1.16 (m, 8H).

Step 3: Synthesis of 4-[8-[[4-[(6-chloro-3-pyridyl)methoxy]-3-methoxy-phenyl]methyl-[2-(3,4-dimethoxyphenyl)ethyl]amino]octylamino]-2-(2,6-dioxo-3-piperidyl) isoindoline-1,3-dione (Compound 6)

To a solution of 8-[[2-(2,6-dioxo-3-piperidyl)-1,3-dioxoisoindolin-4-yl]amino]octyl 4-methylbenzenesulfonate (275.98 mg, 496.68 μmol) and N-[[4-[(6-chloro-3-pyridyl)methoxy]-3-methoxy-phenyl]methyl]-2-(3,4-dimethoxyphenyl) ethanamine (200 mg, 451.53 μmol) in dioxane (2 mL) were added DIPEA (175.07 mg, 1.35 mmol, 235.95 μL) and NaI (13.54 mg, 90.31 μmol, 0.2 eq) at 25° C. The reaction mixture was heated to 100° C. for 16 hours. LCMS showed the 8-[[2-(2,6-dioxo-3-piperidyl)-1,3-dioxo-isoindolin-4-yl]amino]octyl 4-methylbenzenesulfonate was consumed completely and a main peak with desired mass. The mixture solution was concentrated under reduced pressure. The crude product was purified with prep-HPLC (column: Phenomenex Gemini-NX $C_{18}$ 75*30 mm*3 um; mobile phase: [water (10 mM $NH_4HCO_3$)-ACN]; B %: 55%-85%, 8 min) and lyophilized to afford 4-[8-[[4-[(6-chloro-3-pyridyl) methoxy]-3-methoxy-phenyl]methyl-[2-(3,4-dimethoxyphenyl)ethyl]amino]octylamino]-2-(2,6-dioxo-3-piperidyl) isoindoline-1,3-dione (114.4 mg, 138.44 μmol, 30.66% yield, 100% purity) as yellow solid. $MS(M+H)^+$=825.9

$^1$H NMR (400 MHz, $CDCl_3$) δ=8.45 (d, J=2.4 Hz, 1H), 8.14 (br s, 1H), 7.77 (dd, J=2.6, 8.3 Hz, 1H), 7.49 (dd, J=7.2, 8.4 Hz, 1H), 7.34 (d, J=8.4 Hz, 1H), 7.09 (d, J=7.2 Hz, 1H), 6.96-6.84 (m, 2H), 6.83-6.74 (m, 3H), 6.72-6.62 (m, 2H), 6.22 (br t, J=5.4 Hz, 1H), 5.10 (s, 2H), 4.97-4.82 (m, 1H), 3.93-3.78 (m, 9H), 3.57 (s, 2H), 3.33-3.16 (m, 2H), 2.93-2.84 (m, 1H), 2.80-2.75 (m, 1H), 2.73-2.68 (m, 3H), 2.47 (br s, 2H), 2.19-2.07 (m, 1H), 1.68-1.25 (m, 5H), 1.49-1.45 (m, 1H), 1.43-1.36 (m, 2H), 1.35-1.21 (m, 6H).

Experimental Examples

1. Culture of HeLa Cell Line

The HeLa cell line was purchased from Korea Cell Line Bank (KCLB), Seoul, Korea. The passage in cell culture was maintained at P115 to P125.

For cell counting, cell counter (Thermo Fisher Scientific Inc., Catalog #AMQAX1000) and 0.4% trypan blue solution were used.

For cell culture, DMEM (Gibco, Cat. No. 1195-65; Lot. No. 2085318), FBS (Gibco, Cat. No. 16000-044; Lot. No. 2097593), Penicillin/Streptomycin (PS) (Gibco, Cat. No. 15140-122; Lot. No. 2058855), 100 $mm^2$ cell culture dish (SPL, Cat. No. 20100), 150 $mm^2$ cell culture dish (SPL, Cat. No. 20150), 12-well culture plate (SPL, Cat. No. 30012), PBS pH 7.4 (Gibco, Cat. No. 10010-023; Lot. No. 2085080), TrypLE™ Express (Gibco, Cat. No. 12605-010; Lot No. 2070638), Counting Chamber (Hematocytometer) (Hirschmann, Cat. No. 8100204), and 0.4% Trypan Blue Solution (DYNEBIO, Cat. No. CBT3710; Lot. No. 20190723) were used.

2. Treatment of Compounds of the Present Invention $2\times10^5$ cells were seeded for each well of a 12-well plate (SPL), and the cells were cultured in the culture medium in a total volume of 2 mL.

The compounds of Examples were completely dissolved in DMSO and used in the experiment, and thymidine was completely dissolved in DW and used in the experiment. For thymidine block, the products were treated with 2 mM of thymidine (Sigma-Aldrich Cat. No. T9250-5G) and then incubated for 24 hours.

For release and chemical treatment, the medium was suctioned and washed 3 times with 1×PBS. Complete media was added, followed by incubation for 4 hours in a $CO_2$ incubator. Each compound was treated according to the concentration of 100 nM and then incubated for 6 hours again.

3. Western Blotting

For SDS-PAGE and Western blotting, 1×RIPA lysis buffer (Rockland, Cat. No. MB-030-0050; Lot no. 39751), 100× Protease Inhibitor Cocktail (Quartett, Cat. No. PPI1015; Lot no. PC050038424), Pierce™ BCA protein assay kit (ThermoScientific, Cat. No. 23225; Lot no. UC276876), albumin standard (ThermoScientific, Cat. No. 23209; Lot no. UB269561), 4-15% Mini-PROTEAN TGX stain-free gel (Bio-rad, Cat. No. 4568085; Lot no. L007041B), 10× Tris/Glycine/SDS buffer (Bio-rad, Cat. No. 1610732; Lot no. 10000044375B); 10×TBS (Bio-rad, Cat. No. 1706435; Lot no. 1000045140B), 10% Tween 20 (Cat. No. 1610781; Lot no. L004152B), Color protein standard broad range (NEB, Cat. No. P7719S; Lot no. 10040349), 4× Laemmli sample buffer (Bio-rad, Cat. No. 1610747; Lot no. L004133B), β-mercaptoethanol (Sigma-Aldrich, Cat. No. M3148; Lot no. 60-24-2), SuperBlock™ T20 (TBS) blocking buffer (ThermoScientific, Cat. No. 37536; Lot no. UC282578), 1M sodium azide solution (Sigma-Aldrich, Cat. No. 08591-1mL-F; Lot no. BCBV4989), α-Rabbit pAb to Ms IgG (abcam, Cat. No. ab97046; Lot no. GR3252115-1), α-Goat pAb to Rb IgG (CST, Cat. No. 7074S; Lot no. 28), α-GAPDH (abcam, Cat. No. ab8245; Lot no. GR3275542-2), α-Plk1 (CST, Cat. No. 208G4), α-BRD4 (CST, Cat. No. 13440S), ECL™ Prime western blotting reagents (GE Healthcare, Cat. No. RPN2232; Lot no. 17001655), Ponceau S solution (Sigma-Aldrich, Cat. No. P7170; Lot no. SLBV4112), Difco™ Skim milk (BD, Cat. No. 232100; Lot no. 8346795), and iBlot® 2 NC Regular stacks (Invitrogen, Cat. No. IB23001; Lot no. 2NR110619-02) were used.

For cell harvesting, the cells were first separated from the plate using trypsin and then washed with the medium and PBS. Specifically, the medium was suctioned off and washed with 1 mL of PBS, and PBS was suctioned off. The cells were treated with 0.5 mL TrypLE™ Express at 37° C. for 7 minutes to separate the cells, and then 0.5 mL of complete medium was added to collect 1 mL of cell culture solution. Then, 1 mL of the cell collection solution was centrifuged at 8,000 rpm for 120 seconds, and the supernatant was removed. After washing with 0.2 mL of PBS, the PBS was removed.

For cell lysis, a lysis buffer was added and cell debris was removed to obtain a cell lysate. Specifically, the cells were treated with 70 μL of 1×RIPA buffer containing a protease inhibitor and incubated for 30 minutes on ice. Then, the cells were centrifuged at 4° C. and 15,000 rpm for 10 minutes to obtain a cell lysate.

Then, a standard curve was obtained using the BCA assay, and the protein mass in the lysate was quantified by substituting the curve equation. The mixture was incubated at 37° C. for 30 minutes using 20 μL of standard or sample solution, and 200 μL of BCA or Bradford solution, and measured at 562 nm absorbance. Samples were prepared by adding 4× sample buffer so that the quantity of protein added to each well was 15 μg.

Sodium dodecyl sulfate polyacrylamide gel electrophoresis (SDS-PAGE) was performed by setting a running time of 100 minutes at 120 V on a 4-15% Mini-PROTEAN TGX stain-free gel (15 well). Transferring was performed on iBlot® 2 NC Mini stacks at PO mode of the dry blotting system. After staining using Ponceau S solution, blocking was performed for 1 hour with a blocking buffer (Thermo). After washing with 1×TBS containing 0.05% Tween 20, the product was reacted at 4° C. for 16 hours with anti-Plk1 (CST) antibody (1:500), anti-BRD4 (Cell signaling) antibody (1:1000) or anti-GAPDH(abcam) antibody (1:10,000) in 1×TBS-T as a primary antibody. After washing three times for 10 minutes with 1×TBS containing 0.05% Tween20, the product was reacted at room temperature for 1 hour with anti-mouse antibody (abcam) (1:10000) or anti-rabbit antibody (CST) (1:5000) in 1×TBS-T as a secondary antibody. Then, after washing three times for 10 minutes with 1×TBS containing 0.05% Tween 20, the product was detected with an ECL working solution (1:1).

To analyze the results, an image analyzer (GE) was used to obtain final blot data. The ratio of PLK1 to GAPDH for each sample was calculated using the ImageQuant TL (ver.8.2.0) program. Each calculated value was entered into each cell of the Graphpad Prism 9 program, and the graph was automatically calculated to confirm the Dmax value corresponding to the protein degradation ability.

4. Confirmation of PLK1 Degradability of the Compounds of the Present Invention

As a result of the experiment, it was confirmed that all the compounds of the examples of the present invention exhibited a PLK1 degradability of 40 to 60%.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the disclosure described herein. Such equivalents are intended to be encompassed by the following claims. It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

The invention claimed is:

1. A compound represented by Formula I, a stereoisomer thereof, or a pharmaceutically acceptable salt thereof:

Formula (I)

PTM—linker—ULM wherein

PTM is PLK1 binding moiety represented by Formula (II):

Formula (II)

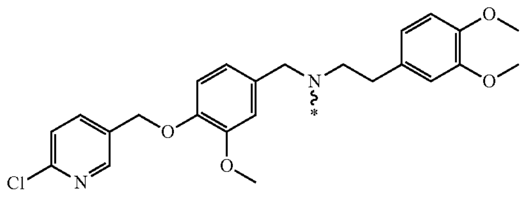

wherein ∿∿∿* indicates the attachment point of the linker;

ULM is CRBN E3 ubiquitin ligase binding moiety represented by Formula (A):

Formula (A)

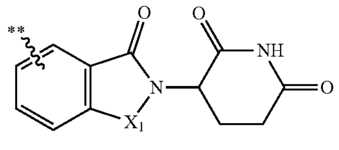

wherein $X_1$ is $—CH_2—$ or —CO—; and

∿∿∿ ** indicates the attachment point of the linker; and the linker is $*—(CH_2CH_2O)_p—CH_2CH_2—NH—**$ or $*—(CH_2CH_2CH_2)_q—CH_2CH_2—NH—**$;

wherein p is an integer from 1 to 4;

q is an integer from 1 to 4; and

* and ** indicate the attachment points of the linker to the PTM and ULM moieties, respectively.

2. The compound of claim 1, wherein the compound is a compound selected from Compound 1

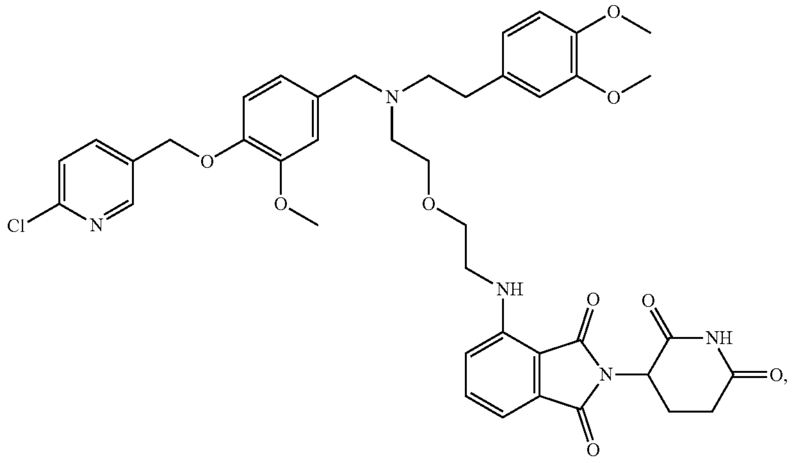

Compound 2

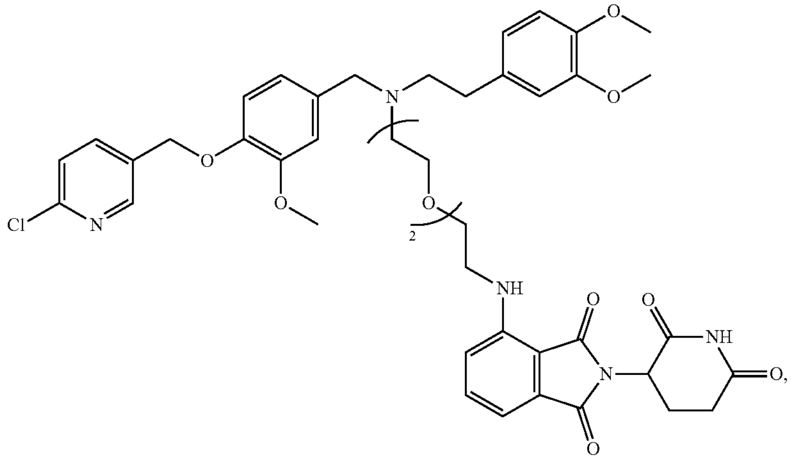

Compound 3

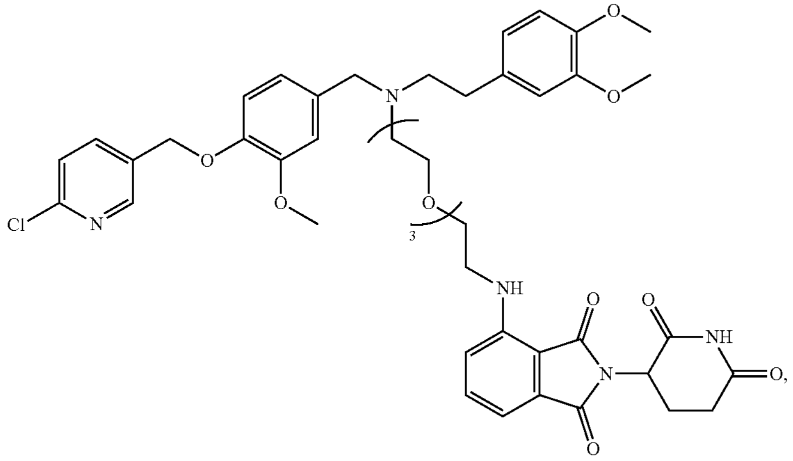

-continued
Compound 4
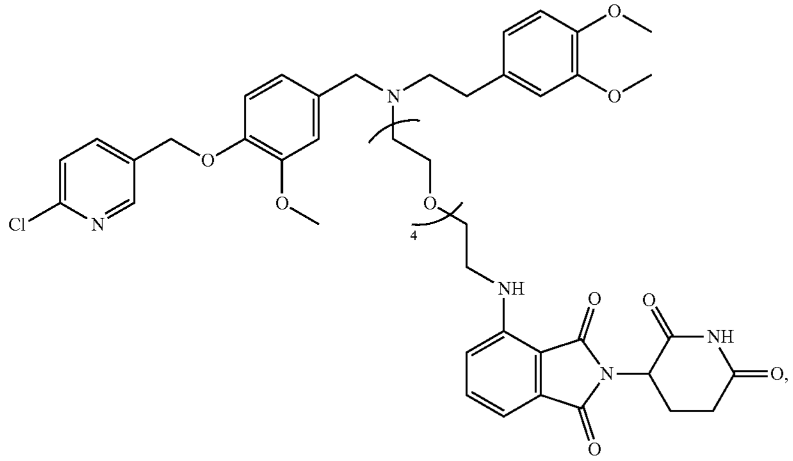
, or
Compound 6
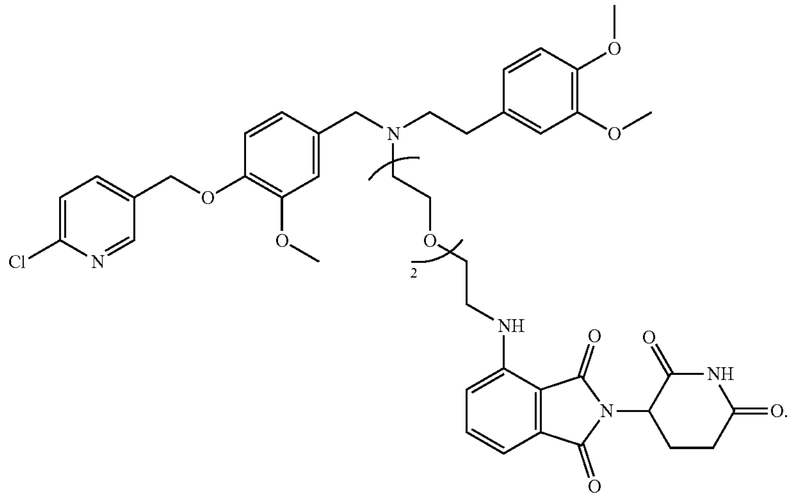
.
3. The compound of claim 1, wherein the compound is a bifunctional compound that induces PLK1 protein degradation.
* * * * *